(12) United States Patent
Mishra et al.

(10) Patent No.: US 8,637,683 B2
(45) Date of Patent: Jan. 28, 2014

(54) MACROCYCLIC LACTONE DERIVATIVES FOR THE TREATMENT OF CANCER

(75) Inventors: Prabhu Dutt Mishra, Maharashtra (IN); Shafee Mohammed Abdul, Andhra Pradesh (IN); Ram Vishwakarma, Jammu (IN); Heinz-Herbert Fiebig, Freiburg (DE); Gerhard Kelter, Ehrenkirchen (DE)

(73) Assignees: Piramal Enterprises Limited, Mumbai (IN); Oncotest GmbH, Freiburg (DE)

( * ) Notice: Subject to any disclaimer, the term of this patent is extended or adjusted under 35 U.S.C. 154(b) by 0 days.

(21) Appl. No.: 13/510,458

(22) PCT Filed: Nov. 15, 2010

(86) PCT No.: PCT/IB2010/055161
§ 371 (c)(1), (2), (4) Date: May 17, 2012

(87) PCT Pub. No.: WO2011/061666
PCT Pub. Date: May 26, 2011

(65) Prior Publication Data
US 2012/0245183 A1 Sep. 27, 2012

Related U.S. Application Data

(60) Provisional application No. 61/261,856, filed on Nov. 17, 2009.

(51) Int. Cl.
*C07D 313/00* (2006.01)

(52) U.S. Cl.
USPC .......................................... 549/266

(58) Field of Classification Search
USPC .......................................... 549/266
See application file for complete search history.

(56) References Cited

FOREIGN PATENT DOCUMENTS

WO 97/23475 A1 7/1997

OTHER PUBLICATIONS

Kinashi et al. Tetrahedron Letters. 1981, 22 (59), 3857-3890.*
Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000).*
Huss, Markus et al., "Inhibitors of V-ATPases: old and new players", The Journal of Experimental Biology, vol. 212, 2009, pp. 341-346, cited in ISR.
Kinashi, Haruyashu et al., "Alkaline Degradation Products of Concanamycin A", Tetrahedron Letters, vol. 22, No. 39, 1981, pp. 3857-3860, cited in ISR.
International Search Report of PCT/IB2010/055161, mailing date of Apr. 14, 2011.
Written Opinion of PCT/IB2010/055161, mailing date of Apr. 14, 2011.
Yoshimoto, Yuya et al., "Vacuolar-type H+-ATPase Inhibitory Activity of Synthetic Analogues of the Concanamycins: Is the Hydrogen Bond Network Involving the Lactone Carbonyl, the Hemiacetal Hydroxy Group, and the C-19 Hydroxy Group Essential for the Biological Activity of the Concanamycins?", Bioorganic & Medicinal Chemistry Letters vol. 12, p. 3525-3528, Sep. 21, 2002, cited in specification (4 pages).
Woo, Je-Tae et al., "Isolation, Characterization and Biological Activities of Concanamycins as Inhibitors of Lysosomal Acidication", The Journal of Antibiotics, vol. 45, No. 7, p. 1108-1116, Jan. 30, 1992, cited in specification (9 pages).
Dengler, Wolfgang A. et al., "Development of a propidium iodide fluorescence assay for proliferation and cytotoxicity assays", Anti-Cancer Drugs, vol. 6, p. 522-532 (1995), cited in specification (11 pages).

* cited by examiner

*Primary Examiner* — Nizal Chandrakumar
(74) *Attorney, Agent, or Firm* — Westerman, Hattori, Daniels & Adrian, LLP

(57) ABSTRACT

The present invention provides compounds represented by formula (1): wherein, $R_1$, $R_2$, $R_3$ and $R_4$ are as defined in the specification, in all their stereoisomeric and tautomeric forms and mixtures thereof in all ratios, and their pharmaceutically acceptable salts, pharmaceutically acceptable solvates, pharmaceutically acceptable polymorphs and prodrugs. The invention also relates to processes for the manufacture of compounds of formula (1) and pharmaceutical compositions containing them. The compounds and the pharmaceutical compositions of the present invention are useful for the treatment of cancer. The present invention further provides a method of treatment of cancer by administering a therapeutically effective amount of the said compound of formula (1) or its pharmaceutical composition, to a mammal in need thereof.

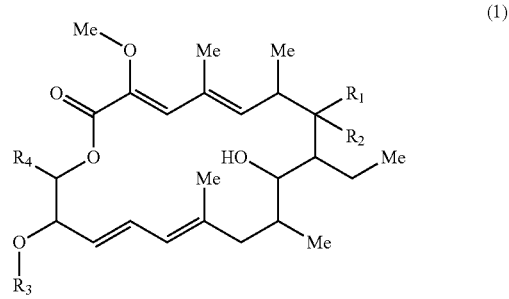

(1)

17 Claims, No Drawings

MACROCYCLIC LACTONE DERIVATIVES FOR THE TREATMENT OF CANCER

CROSS-REFERENCE TO RELATED APPLICATION

This application is related to our copending PCT application entitled: "USE OF MACROCYCLIC LACTONE DERIVATIVES FOR THE TREATMENT OF INFLAMMATORY DISORDERS", filed on the same date as the present application.

FIELD OF THE INVENTION

The present invention relates to macrocyclic lactone derivatives, to processes for their preparation, pharmaceutical compositions containing them, and their use for the treatment of cancer.

BACKGROUND OF THE INVENTION

Cancer is an uncontrolled growth and spread of cells that may affect almost any tissue of the body. It is caused due to a deregulation of the signaling pathways involved in cell survival, cell proliferation and cell death. More than eleven million people are diagnosed with cancer every year. It is estimated that there will be sixteen million new cases every year by 2020. Cancer causes seven million deaths every year worldwide.

Current treatments for cancer have limited effectiveness and a number of side effects. Cancer therapy currently includes surgery, radiation therapy, chemotherapy, bone marrow transplantation, stem cell transplantation, hormonal therapy, immunotherapy, antiangiogenic therapy, targeted therapy, gene therapy and others.

In the treatment of cancer, chemical compounds are used to reduce, inhibit, or diminish the proliferation of tumor cells, and thereby assist in reducing the size of a tumor. These compounds, which exhibit antitumor activity, find use in the treatment of cancers.

Biorganic and Medicinal Chemistry Letters (12, 3525-3528, (2002)), describes synthetic analogs of concanamycins which induce apoptosis to cancer cells that overexpress epidermal growth factor receptors (EGFR).

The present invention describes new macrocyclic lactone derivatives for the treatment of cancer.

SUMMARY OF THE INVENTION

The present invention relates to macrocyclic lactone derivatives, which are useful in the treatment of cancer.

Thus according to one aspect of the present invention, there is provided a compound of formula (1) (as provided herein below), as well as a stereoisomer, tautomer, pharmaceutically acceptable salt, solvate, polymorph or prodrug thereof.

According to a further aspect of the present invention, there are provided processes for the preparation of compounds of formula (1).

According to a further aspect, there is provided the use of compound of formula (1) for the treatment of cancer.

According to another aspect of the present invention, there are provided pharmaceutical compositions including compound of formula (1) as active ingredient.

According to another aspect of the present invention, there is provided a method for the treatment of cancer, the method including administering to a mammal in need thereof a therapeutically effective amount of compound of formula (1).

According to another aspect of the present invention, there are provided methods for the manufacture of medicaments including compound of formula (1), which are useful for the treatment of cancer.

DETAILED DESCRIPTION OF THE INVENTION

The present invention provides compounds represented by the following formula (1):

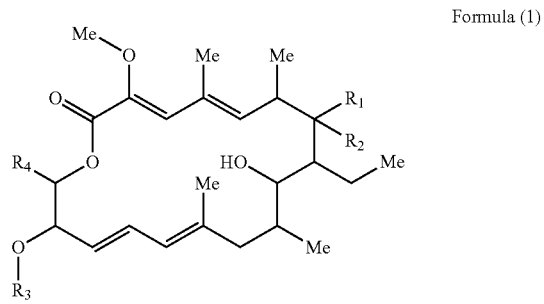

Formula (1)

and all of their stereoisomeric and tautomeric forms and mixtures thereof, in all ratios, and their pharmaceutically acceptable salts, pharmaceutically acceptable solvates, pharmaceutically acceptable polymorphs and prodrugs, wherein, $R_1$ is selected from halogen, hydroxy, alkoxy, —O(CO)$R_{13}$, —S$R_{14}$, and —N$R_{14}R_{15}$;

$R_2$ is hydrogen; or optionally $R_1$ is absent and $R_2$ is =O;

$R_3$ is alkyl;

$R_4$ is selected from the following formulae:

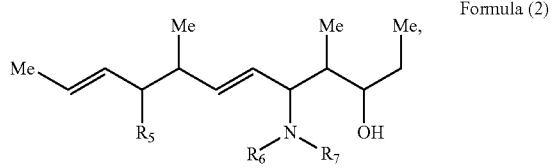

Formula (2)

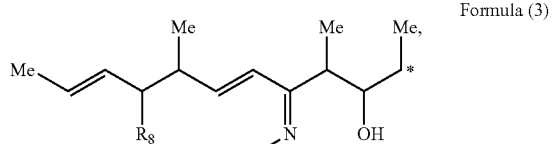

Formula (3)

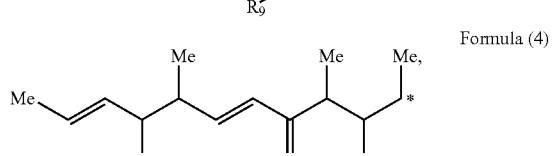

Formula (4)

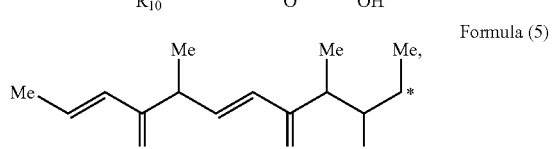

Formula (5)

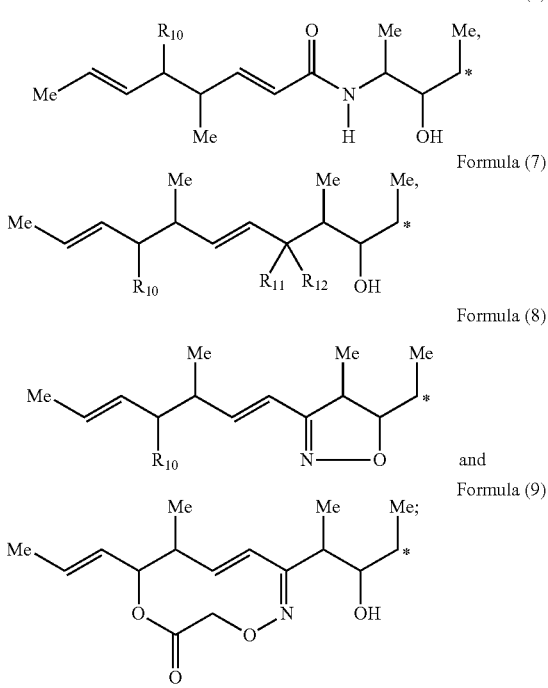

\* indicates point of attachment
R$_5$ is selected from hydroxy, and alkoxy;
R$_6$ is selected from hydrogen, hydroxy, alkyl, and alkoxy;
R$_7$ is selected from hydrogen, alkyl, and —(CO)R$_{16}$;
R$_8$ is selected from hydroxy, and alkoxy;
R$_9$ is selected from hydroxy, alkyl, alkoxy, aryl, aralkyl, aryloxy, benzyloxy, heterocyclyl, —O-heterocyclyl, —OCH$_2$COOR$_{17}$, and —OCH$_2$COR$_{18}$;
R$_{10}$ is selected from halogen, hydroxy, alkoxy, —SR$_{14}$, —NR$_{14}$R$_{15}$, and —O(CO)R$_{19}$;
R$_{11}$ is selected from hydrogen, and halogen;
R$_{12}$ is selected from hydrogen, halogen, and hydroxy;
R$_{13}$ is selected from alkyl, and aryl;
R$_{14}$ is selected from hydrogen, alkyl, aralkyl, aryl, and heterocyclyl;
R$_{15}$ is selected from hydrogen, and alkyl;
R$_{16}$ is selected from alkyl, and aryl;
R$_{17}$ is selected from hydrogen, and alkyl;
R$_{18}$ is selected from alkyl, —NHCH$_2$R$_{20}$, aryl, and heterocyclyl;
R$_{19}$ is selected from alkyl, aralkyl, aryl, and heterocyclyl; and
R$_{20}$ is selected from hydrogen, alkyl, aryl, and heterocyclyl;
with the proviso that,
when R$_1$ is hydroxy; R$_2$ is hydrogen; R$_3$ is methyl; and R$_4$ is formula (4):

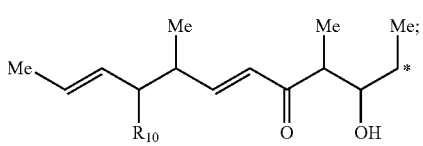

then R$_{10}$ is not a hydroxy group.
where alkyl is unsubstituted or substituted by one or two of the same or different groups selected from: hydroxy, halogen, amino, hydroxyalkyl, alkoxy, aryl, aryloxy, and heterocyclyl;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, alkoxy, aryl, and heterocyclyl;
heterocyclyl is unsubstituted or substituted by one or two of the same or different groups selected from: halogen, hydroxy, amino, alkyl, hydroxyalkyl, alkoxy, aryl, and heterocyclyl.

DEFINITIONS

Listed below are definitions, which apply to the terms as they are used throughout the specification and the appended claims (unless they are otherwise limited in specific instances), either individually or as part of a larger group.

As used herein, the term "alkyl" whether used alone or as part of a substituent group, refers to saturated aliphatic groups, including straight or branched-chain containing from 1 to 6 carbon atoms. Suitable alkyl groups contain for example, from 1 to 4 carbon atoms, such as methyl, ethyl, propyl, isopropyl, n-butyl, isobutyl, and t-butyl. An alkyl group is optionally substituted by one or more identical or different substituents. Any kind of substituent present in substituted alkyl groups can be present in any desired position provided that the substitution does not lead to an unstable molecule. A substituted alkyl refers to an alkyl group in which one or more, for example, 1, 2, 3, 4 or 5 hydrogen atoms are replaced with substituents, for example, halogen, hydroxy, amino, alkoxy, hydroxyalkyl, aryloxy, acyloxy, aryl, heteroaryl, or heterocyclyl group.

As used herein, the term "alkoxy" refers to an alkyl group having an oxygen attached thereto, wherein alkyl is as defined above. Representative alkoxy groups include methoxy, ethoxy, propoxy, and tert-butoxy group. The terms include, therefore, alkoxy groups, which are substituted by one or more identical or different groups selected from: halogen, hydroxy, alkyl, and hydroxyalkyl.

As used herein, the term "aryl" refers to a monocyclic or bicyclic hydrocarbon group having up to 10 ring carbon atoms, in which at least one carbocyclic ring is present that has a conjugated π electron system. Examples of aryl group include phenyl and naphthyl. A substituted aryl refers to an aryl group, which is substituted by one or more substituents, for example, up to five identical or different substituents selected from the group consisting of halogen, hydroxy, amino, alkyl, hydroxyalkyl, alkoxy, aryloxy, aryl, and a heterocyclyl group. Aryl groups can be substituted in any desired position. For example, in monosubstituted phenyl groups, the substituent can be located in the 2-position, the 3-position, the 4-position or the 5-position. If the phenyl group carries two substituents, they can be located in 2,3-position, 2,4-position, 2,5-position, 2,6-position, 3,4-position or 3,5-position.

As used herein, the term "aryloxy" refers to the aryl-O— wherein the term aryl is as defined above. Exemplary aryloxy groups include, but are not limited to, phenoxy and naphthoxy.

The term "heteroatom" refers to nitrogen, oxygen and sulfur. It should be noted that any heteroatom with unsatisfied valences is assumed to have a hydrogen atom to satisfy the valences. The ring heteroatoms can be present in any desired number and in any position with respect to each other provided that the resulting heterocyclic system is stable.

The terms "heterocyclyl", and "heterocyclic" refer to a saturated, partially unsaturated or aromatic monocyclic or bicyclic ring system containing 3, 4, 5, 6, 7, 8, 9, or 10, ring atoms of which 1, 2, 3 or 4 are identical or different heteroatoms selected from: nitrogen, oxygen and sulfur. The heterocyclyl group may, for example, have 1 or 2 oxygen atoms and/or 1 or 2 sulfur atoms and/or 1 to 4 nitrogen atoms in the ring. Heterocyclyl includes saturated heterocyclic ring systems, which do not contain any double bonds within the rings, as well as unsaturated heterocyclic ring systems, which contain one or more, up to 5 double bonds within the rings provided that the resulting system is stable. Unsaturated rings may be non-aromatic or aromatic. Aromatic heterocyclyl groups may also be referred to by the customary term "heteroaryl" for which all the definitions and explanations above and below relating to heterocyclyl apply. Monocyclic heterocyclyl groups include 3-membered, 4-membered, 5-membered, 6-membered and 7-membered rings. Suitable examples of such heterocyclyl groups are pyrrolyl, imidazolyl, pyrrolidinyl, pyridinyl, pyrazinyl, pyridazinyl, pyrimidinyl, pyrazolyl, triazolyl, tetrazolyl, piperidinyl, piperazinyl, and morpholinyl. Bicyclic heterocyclyl groups include two fused rings, one of which is 5-, 6- or 7-membered heterocyclic ring and the other of which is a 5-, 6- or 7-membered carbocyclic or heterocyclic ring. Exemplary bicyclic heterocyclic groups include benzoxazolyl, quinolyl, isoquinolyl, indolyl, isoindolyl, and benzofurazanyl.

A substituted heterocyclyl refers to a heterocyclyl group which is substituted with one or more (up to 5), identical or different substituents. Examples of substituents for the ring carbon and ring nitrogen atoms are: halogen, hydroxy, amino, alkyl, hydroxyalkyl, alkoxy, aryloxy, aryl, and heterocyclyl. The substituents can be present at one or more positions provided that a stable molecule results.

As used herein the term "aralkyl" refers to an alkyl group substituted with an aryl or heteroaryl group, wherein the terms alkyl, aryl and heteroaryl are as defined above. Exemplary aralkyl groups include —(CH$_2$)$_p$-phenyl, —(CH$_2$)$_p$-pyridyl, wherein p is an integer from 1 to 3. The aralkyl group may be further substituted with hydroxy, halogen, amino, alkyl, aryl or heteroaryl.

As used herein, the term —O-heterocyclyl refers to the heterocyclic ring attached directly to an oxygen atom, wherein the term heterocyclyl is as defined above.

The term "halogen" refers to fluorine, chlorine, bromine or iodine.

The term "amino" refers to unsubstituted, mono-substituted and di-substituted amino groups. As used herein, the terms mono- or di-substituted amino refer respectively to an amino group substituted by one or two groups which may be the same or different. The substituents on the amino group are independently selected from: alkyl, hydroxyalkyl aralkyl, aryl, and heterocyclyl. It will be understood by those skilled in the art that the moieties on the amino group can themselves be substituted, if appropriate.

It will be understood that "substitution" or "substituted with" includes the implicit proviso that such substitution is in accordance with permitted valence of the substituted atom and the substituent, as well as results in a stable compound, which does not readily undergo transformation such as by rearrangement, cyclization, elimination, etc.

EMBODIMENTS OF THE INVENTION

The present invention provides compounds represented by the following formula (1),

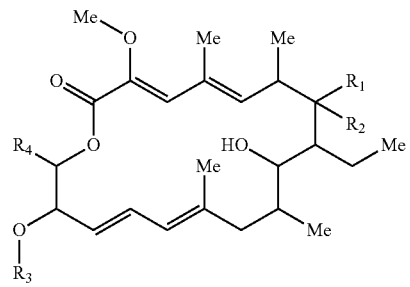

Formula (1)

and all of their stereoisomeric and tautomeric forms and mixtures thereof, in all ratios, and their pharmaceutically acceptable salts, pharmaceutically acceptable solvates, pharmaceutically acceptable polymorphs and prodrugs, wherein, $R_1$ is selected from halogen, hydroxy, alkoxy, —O(CO)$R_{13}$, —S$R_{14}$, and —N$R_{14}R_{15}$;

$R_2$ is hydrogen;

$R_3$ is alkyl;

$R_4$ is selected from the following formulae:

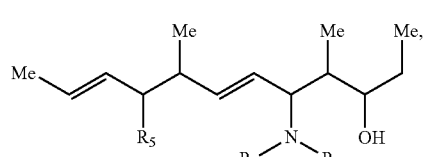

Formula (2)

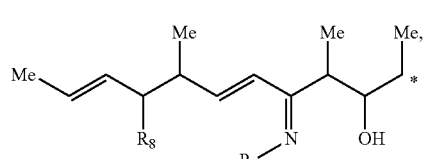

Formula (3)

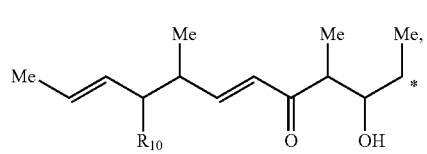

Formula (4)

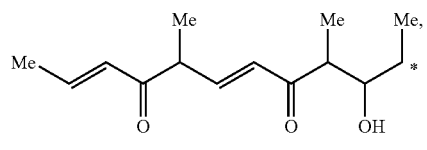

Formula (5)

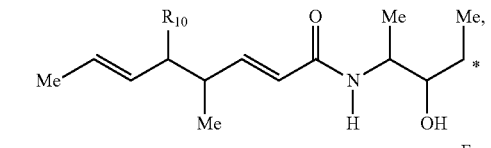

Formula (6)

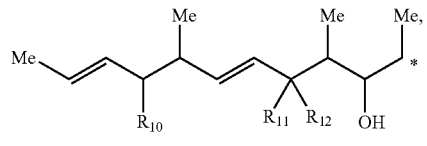

Formula (7)

-continued

Formula (8)

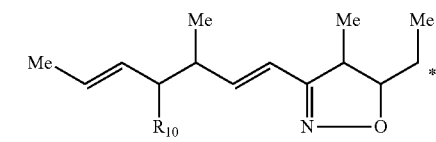

and

Formula (9)

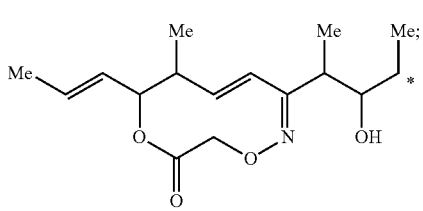

* indicates point of attachment
$R_5$ is selected from hydroxy, and alkoxy;
$R_6$ is selected from hydrogen, hydroxy, alkyl, and alkoxy;
$R_7$ is selected from hydrogen, alkyl, and —(CO)$R_{16}$;
$R_8$ is selected from hydroxy, and alkoxy;
$R_9$ is selected from hydroxy, alkyl, alkoxy, aryl, aralkyl, aryloxy, benzyloxy, heterocyclyl, —O-heterocyclyl, —OCH$_2$COOR$_{17}$, and —OCH$_2$COR$_{18}$;
$R_{10}$ is selected from halogen, hydroxy, alkoxy, —SR$_{14}$, —NR$_{14}$R$_{15}$, and —O(CO)R$_{19}$;
$R_{11}$ is selected from hydrogen, and halogen;
$R_{12}$ is selected from hydrogen, halogen, and hydroxy;
$R_{13}$ is selected from alkyl, and aryl;
$R_{14}$ is selected from hydrogen, alkyl, aralkyl, aryl, and heterocyclyl;
$R_{15}$ is selected from hydrogen, and alkyl;
$R_{16}$ is selected from alkyl, and aryl;
$R_{17}$ is selected from hydrogen, and alkyl;
$R_{18}$ is selected from alkyl, —NHCH$_2$R$_{20}$, aryl, and heterocyclyl;
$R_{19}$ is selected from alkyl, aralkyl, aryl, and heterocyclyl; and
$R_{20}$ is selected from hydrogen, alkyl, aryl, and heterocyclyl;
with the proviso that,
when $R_1$ is hydroxy; $R_2$ is hydrogen; $R_3$ is methyl; and
$R_4$ is formula (4):

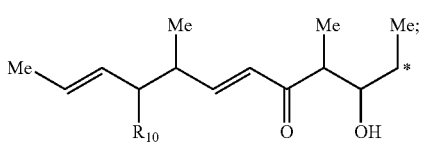

then $R_{10}$ is not a hydroxy group.
where alkyl is unsubstituted or substituted by one or two of the same or different groups selected from: hydroxy, halogen, amino, hydroxyalkyl, alkoxy, aryl, aryloxy, and heterocyclyl;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, alkoxy, aryl, and heterocyclyl;
heterocyclyl is unsubstituted or substituted by one or two of the same or different groups selected from: halogen, hydroxy, amino, alkyl, hydroxyalkyl, alkoxy, aryl, and heterocyclyl.

In one embodiment, the present invention provides compounds represented by formula (1), wherein,
$R_1$ is selected from halogen, hydroxy, and alkoxy;
$R_2$ is hydrogen;
$R_3$ is alkyl;
$R_4$ is formula (3):

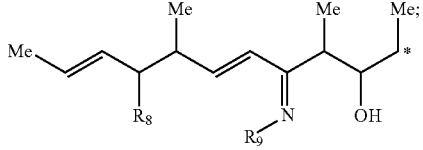

* indicates point of attachment
$R_8$ is hydroxy;
$R_9$ is selected from hydroxy, alkyl, alkoxy, aryl, aralkyl, aryloxy, benzyloxy, —OCH$_2$COOR$_{17}$, and —OCH$_2$COR$_{18}$;
$R_{17}$ is selected from hydrogen, and alkyl;
$R_{18}$ is selected from alkyl, —NHCH$_2$R$_{20}$, aryl, and heterocyclyl; and
$R_{20}$ is selected from hydrogen, alkyl, aryl, and heterocyclyl;
where alkyl is unsubstituted or substituted by one or two of the same or different groups selected from: hydroxy, halogen, amino, hydroxyalkyl, alkoxy, aryl, aryloxy, and heterocyclyl;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, alkoxy, aryl, and heterocyclyl;
heterocyclyl is unsubstituted or substituted by one or two of the same or different groups selected from: halogen, hydroxy, amino, alkyl, hydroxyalkyl, alkoxy, aryl, and heterocyclyl.

In a further embodiment, the present invention provides compounds represented by formula (1), wherein,
$R_1$ is hydroxy;
$R_2$ is hydrogen;
$R_3$ is alkyl;
$R_4$ is formula (3):

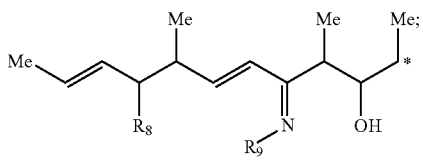

* indicates point of attachment
$R_8$ is hydroxy; and
$R_9$ is selected from hydroxy, alkyl, alkoxy, and benzyloxy;
where alkyl is unsubstituted or substituted by one or two of the same or different groups selected from: hydroxy, halogen, amino, hydroxyalkyl, and alkoxy.

In a further embodiment, the present invention provides compounds represented by formula (1), wherein,
$R_1$ is hydroxy;
$R_2$ is hydrogen;
$R_3$ is methyl;
$R_4$ is formula (3):

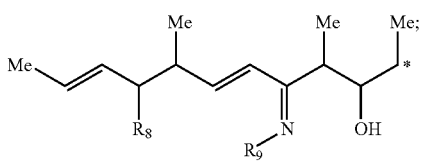

* indicates point of attachment
$R_8$ is hydroxy; and
$R_9$ is selected from hydroxy, methoxy, and benzyloxy.

In a further embodiment, the present invention provides compound represented by formula (1), wherein,
$R_1$ is hydroxy;
$R_2$ is hydrogen;
$R_3$ is methyl;
$R_4$ is formula (3):

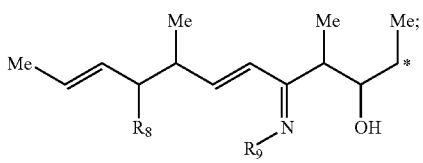

* indicates point of attachment
$R_8$ is hydroxy; and
$R_9$ is hydroxy.

In one embodiment, the present invention provides compounds represented by formula (1), wherein,
$R_1$ is selected from halogen, hydroxy, and alkoxy;
$R_2$ is hydrogen;
$R_3$ is alkyl;
$R_4$ is formula (3):

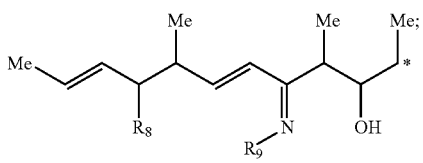

* indicates point of attachment
$R_8$ is selected from hydroxy, and alkoxy;
$R_9$ is selected from —$OCH_2COOR_{17}$, and —$OCH_2COR_{18}$;
$R_{17}$ is selected from hydrogen, and alkyl;
$R_{18}$ is selected from alkyl, heterocyclyl and —$NHCH_2R_{20}$; and
$R_{20}$ is selected from hydrogen, alkyl, aryl, and heterocyclyl;
where alkyl is unsubstituted or substituted by one or two of the same or different groups selected from: hydroxy, halogen, amino, hydroxyalkyl, and alkoxy;
alkoxy is unsubstituted or substituted by one or two of the same or different groups selected from: hydroxy, alkyl, and hydroxyalkyl;
aryl is unsubstituted or substituted by one or two of the same or different groups selected from: halogen, hydroxy, hydroxyalkyl, alkoxy, aryl, and heterocyclyl;
heterocyclyl is unsubstituted or substituted by one or two of the same or different groups selected from: hydroxy, hydroxyalkyl, alkyl, alkoxy, aryl, and heterocyclyl.

In a further embodiment, the present invention provides compounds represented by formula (1), wherein,
$R_1$ is hydroxy;
$R_2$ is hydrogen;
$R_3$ is methyl;
$R_4$ is formula (3):

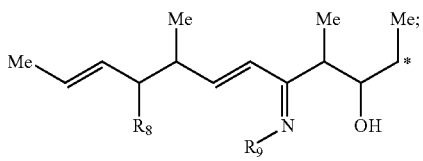

* indicates point of attachment
$R_8$ is hydroxy;
$R_9$ is —$OCH_2COOR_{17}$; and
$R_{17}$ is selected from hydrogen, and alkyl.

In one embodiment, the present invention provides compounds represented by formula (1), wherein,
$R_1$ is hydroxy;
$R_2$ is hydrogen;
$R_4$ is formula (3):

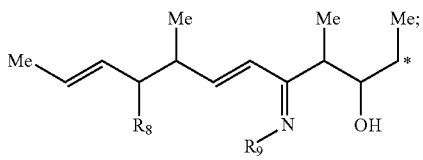

* indicates point of attachment
$R_8$ is hydroxy;
$R_9$ is —$OCH_2COR_{18}$; and
$R_{18}$ is selected from 4-methylpiperazin-1-yl, piperidin-1-yl, and 1,4'-bipiperidin-1'-yl.

In one embodiment, the present invention provides compounds represented by formula (1), wherein,
$R_1$ is hydroxy;
$R_2$ is hydrogen;
$R_3$ is methyl;
$R_4$ is formula (3):

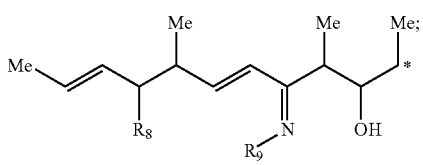

* indicates point of attachment
$R_8$ is hydroxy;
$R_9$ is —$OCH_2COR_{18}$;
$R_{18}$ is —$NHCH_2R_{20}$; and
$R_{20}$ is selected from alkyl, and aryl;
where alkyl is unsubstituted or substituted by one or two of the same or different groups selected from: hydroxy, halogen, amino, hydroxyalkyl, and alkoxy;
aryl is unsubstituted or substituted by one or two of the same or different groups selected from: halogen, hydroxy, and alkoxy.

In one embodiment, the present invention provides compounds represented by formula (1), wherein,
$R_1$ is hydroxy;
$R_2$ is hydrogen;
$R_3$ is methyl;
$R_4$ is formula (3):

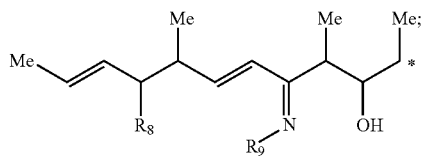

* indicates point of attachment
$R_8$ is hydroxy;
$R_9$ is —OCH$_2$COR$_{18}$;
$R_{18}$ is —NHCH$_2$R$_{20}$; and
$R_{20}$ is selected from —CH$_2$OH, and 4-fluorophenyl.

In another embodiment, the present invention provides compounds represented by formula (1), wherein
$R_1$ is selected from halogen, hydroxy, and alkoxy;
$R_2$ is hydrogen;
$R_3$ is alkyl;
$R_4$ is formula (6):

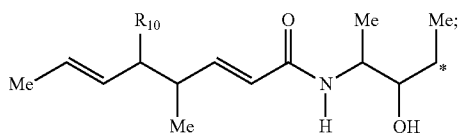

* indicates point of attachment
$R_{10}$ is selected from halogen, hydroxy, and alkoxy;
where alkyl is unsubstituted or substituted by one or two of the same or different groups selected from: hydroxy, halogen, amino, hydroxyalkyl, and alkoxy;
alkoxy is unsubstituted or substituted by one or two of the same or different groups selected from: halogen, hydroxy, alkyl, and hydroxyalkyl.

In one embodiment, the present invention provides compounds represented by formula (1), wherein,
$R_1$ is hydroxy;
$R_2$ is hydrogen;
$R_4$ is formula (6):

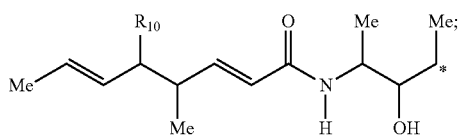

* indicates point of attachment
$R_{10}$ is hydroxy, and alkoxy.

In another embodiment, the present invention provides compounds represented by formula (1), wherein,
$R_1$ is selected from halogen, hydroxy, and alkoxy;
$R_2$ is hydrogen;
$R_3$ is alkyl;
$R_4$ is formula (7):

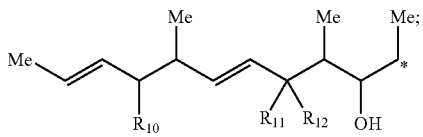

* indicates point of attachment
$R_{10}$ is selected from halogen, hydroxy, and alkoxy;
$R_{11}$ is selected from hydrogen, and halogen; and
$R_{12}$ is selected from hydrogen, halogen, and hydroxy.

In another embodiment, the present invention provides compounds represented by formula (1), wherein,
$R_1$ is hydroxy;
$R_2$ is hydrogen;
$R_3$ is methyl;
$R_4$ is formula (7):

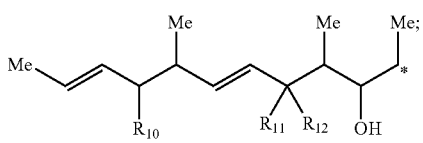

* indicates point of attachment
$R_{10}$ is hydroxy, and alkoxy;
$R_{11}$ is hydrogen; and
$R_{12}$ is hydroxy.

In another embodiment, the present invention provides compounds represented by formula (1), wherein,
$R_1$ is hydroxy;
$R_2$ is hydrogen;
$R_3$ is methyl;
$R_4$ is formula (7):

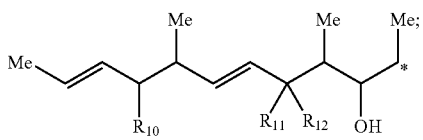

* indicates point of attachment
$R_{10}$ is hydroxy, and alkoxy;
$R_{11}$ is halogen; and
$R_{12}$ is halogen.

In one embodiment, the present invention provides compounds represented by formula (1), wherein,
$R_1$ is selected from halogen, hydroxy, and alkoxy;
$R_2$ is hydrogen;
$R_3$ is alkyl;
$R_4$ is formula (2):

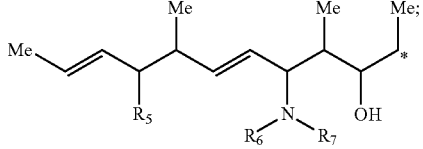

* indicates point of attachment
$R_5$ is selected from hydroxy, and alkoxy;
$R_6$ is selected from hydrogen, alkyl, hydroxy, and alkoxy;

$R_7$ is selected from hydrogen, alkyl, and —(CO)$R_{16}$; and
$R_{16}$ is selected from alkyl, and aryl;
where alkyl is unsubstituted or substituted by one or two of the same or different groups selected from: hydroxy, halogen, amino, hydroxyalkyl, and alkoxy;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, alkoxy, aryl, and heterocyclyl.

In one embodiment, the present invention provides compounds represented by formula (1), wherein,
$R_1$ is selected from halogen, hydroxy, and alkoxy;
$R_2$ is hydrogen;
$R_3$ is alkyl;
$R_4$ is formula (2):

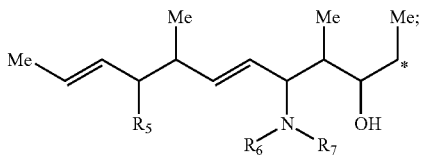

* indicates point of attachment
$R_5$ is selected from hydroxy, and alkoxy;
$R_6$ is selected from hydrogen, and hydroxy;
$R_7$ is selected from hydrogen, alkyl, and —(CO)$R_{16}$; and
$R_{16}$ is alkyl;
where alkyl is unsubstituted or substituted by one or two of the same or different groups selected from: hydroxy, halogen, amino, hydroxyalkyl, and alkoxy;
alkoxy is unsubstituted or substituted by one or two of the same or different groups selected from: halogen, hydroxy, alkyl, and hydroxyalkyl.

In one embodiment, the present invention provides compounds represented by formula (1), wherein,
$R_1$ is hydroxy;
$R_2$ is hydrogen;
$R_3$ is alkyl;
$R_4$ is formula (2):

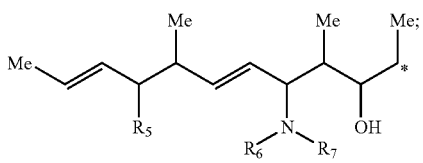

* indicates point of attachment
$R_5$ is selected from hydroxy, and alkoxy;
$R_6$ is hydrogen;
$R_7$ is selected from hydrogen and —(CO)$R_{16}$; and
$R_{16}$ is alkyl.

In one embodiment, the present invention provides compounds represented by formula (1), wherein,
$R_1$ is selected from halogen, hydroxy, alkoxy, —O(CO)$R_{13}$, —S$R_{14}$, and —N$R_{14}R_{15}$;
$R_2$ is hydrogen;
$R_3$ is alkyl;
$R_4$ is formula (4):

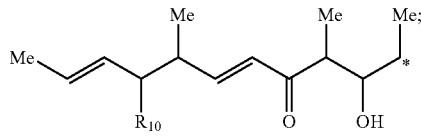

* indicates point of attachment
$R_{10}$ is selected from halogen, hydroxy, alkoxy, —S$R_{14}$, —N$R_{14}R_{15}$, and —O(CO)$R_{19}$;
$R_{13}$ is selected from alkyl, and aryl;
$R_{14}$ is selected from hydrogen, alkyl, aralkyl, aryl, and heterocyclyl;
$R_{15}$ is selected from hydrogen, and alkyl; and
$R_{19}$ is selected from alkyl, aryl, and heterocyclyl;
with the proviso that,
when $R_1$ is hydroxy; $R_2$ is hydrogen; $R_3$ is methyl; and $R_4$ is formula (4):

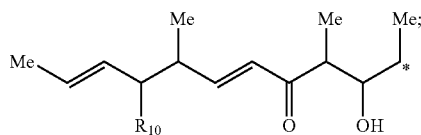

then $R_{10}$ is not a hydroxy group;
where alkyl is unsubstituted or substituted by one or two of the same or different groups selected from: hydroxy, halogen, amino, hydroxyalkyl, alkoxy, aryl, aryloxy, and heterocyclyl;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, alkoxy, aryl, and heterocyclyl;
heterocyclyl is unsubstituted or substituted by one or two of the same or different groups selected from: halogen, hydroxy, amino, alkyl, hydroxyalkyl, alkoxy, aryl, and heterocyclyl.

In one embodiment, the present invention provides compounds represented by formula (1), wherein,
$R_1$ is —S$R_{14}$;
$R_2$ is hydrogen;
$R_3$ is methyl;
$R_4$ is formula (4):

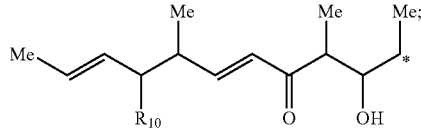

* indicates point of attachment
$R_{10}$ is —S$R_{14}$; and
$R_{14}$ is selected from hydrogen, and alkyl;
where alkyl is unsubstituted or substituted by one or two of the same or different groups selected from: hydroxy, halogen, amino, hydroxyalkyl, and alkoxy.

In one embodiment, the present invention provides compounds represented by formula (1), wherein,
$R_1$ is —N$R_{14}R_{15}$;
$R_2$ is hydrogen;
$R_3$ is alkyl;
$R_4$ is formula (4):

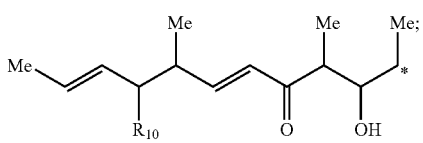

* indicates point of attachment
$R_{10}$ is selected from halogen, hydroxy, alkoxy, —$SR_{14}$, —$NR_{14}R_{15}$, and —$O(CO)R_{19}$;
$R_{14}$ is selected from hydrogen, alkyl, aralkyl, aryl, and heterocyclyl;
$R_{15}$ is selected from hydrogen, and alkyl; and
$R_{19}$ is selected from alkyl, aryl, and heterocyclyl;
where alkyl is unsubstituted or substituted by one or two of the same or different groups selected from: hydroxy, halogen, amino, hydroxyalkyl, alkoxy, aryl, aryloxy, and heterocyclyl;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, and alkoxy;
heterocyclyl is unsubstituted or substituted by one or two of the same or different groups selected from: halogen, hydroxy, amino, alkyl, hydroxyalkyl, and alkoxy.

In one embodiment, the present invention provides compounds represented by formula (1), wherein,
$R_1$ is —$NR_{14}R_{15}$;
$R_2$ is hydrogen;
$R_3$ is alkyl;
$R_4$ is formula (4):

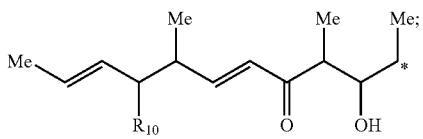

* indicates point of attachment
$R_{10}$ is —$NR_{14}R_{15}$;
$R_{14}$ is selected from hydrogen, and alkyl; and
$R_{15}$ is selected from hydrogen, and alkyl;
where alkyl is unsubstituted or substituted by one or two of the same or different groups selected from: hydroxy, halogen, amino, hydroxyalkyl, and alkoxy;

In one embodiment, the present invention provides compounds represented by formula (1), wherein,
$R_1$ is —$O(CO)R_{13}$;
$R_2$ is hydrogen;
$R_3$ is alkyl;
$R_4$ is formula (4):

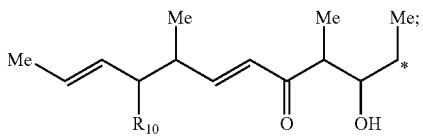

* indicates point of attachment
$R_{10}$ is —$O(CO)R_{19}$;
$R_{13}$ is selected from alkyl, and aryl; and
$R_{19}$ is selected from alkyl, aralkyl, aryl, and heterocyclyl;
where alkyl is unsubstituted or substituted by one or two of the same or different groups selected from: hydroxy, halogen, amino, hydroxyalkyl, and alkoxy;
aryl is unsubstituted or substituted by one or two of the same or different groups selected from: halogen, hydroxy, amino, alkyl, hydroxyalkyl, and alkoxy;
heterocyclyl is unsubstituted or substituted by one or two of the same or different groups selected from: halogen, hydroxy, amino, alkyl, hydroxyalkyl, and alkoxy.

In one embodiment, the present invention provides compounds represented by formula (1), wherein,
$R_1$ is —$O(CO)R_{13}$;
$R_2$ is hydrogen;
$R_3$ is alkyl;
$R_4$ is formula (4):

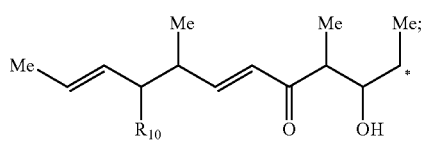

* indicates point of attachment
$R_{10}$ is hydroxy; and
$R_{13}$ is selected from alkyl, and aryl;
where alkyl is unsubstituted or substituted by one or two of the same or different groups selected from: hydroxy, halogen, amino, hydroxyalkyl, and alkoxy;
aryl is unsubstituted or substituted by one or two of the same or different groups selected from: halogen, hydroxy, amino, alkyl, hydroxyalkyl, and alkoxy.

In one embodiment, the present invention provides compounds represented by formula (1), wherein,
$R_1$ is hydroxy;
$R_2$ is hydrogen;
$R_3$ is alkyl;
$R_4$ is formula (4):

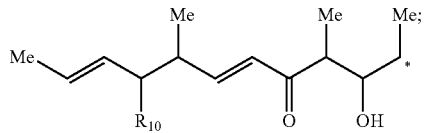

* indicates point of attachment
$R_{10}$ is hydroxy;
with the proviso that,
when $R_1$ is hydroxy; $R_2$ is hydrogen; $R_{10}$ is hydroxy; and $R_4$ is formula (4):

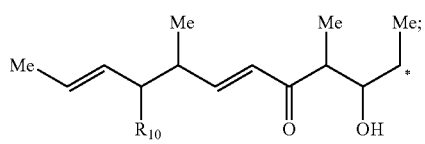

then $R_3$ is not methyl group.

In one embodiment, the present invention provides compounds represented by formula (1), wherein
$R_1$ is hydroxy;
$R_2$ is hydrogen;

$R_3$ is selected from ethyl, propyl, and butyl;
$R_4$ is formula (4):

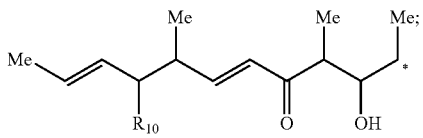

* indicates point of attachment
$R_{10}$ is hydroxy.

In one embodiment, the present invention provides compounds represented by formula (1), wherein,
$R_1$ is halogen;
$R_2$ is hydrogen;
$R_3$ is alkyl;
$R_4$ is formula (4):

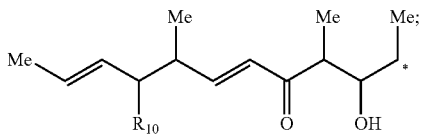

* indicates point of attachment
$R_{10}$ is selected from halogen, hydroxy, alkoxy, —$SR_{14}$, —$NR_{14}R_{15}$ and —$O(CO)R_{19}$;
$R_{14}$ is selected from hydrogen, alkyl, aralkyl, aryl, and heterocyclyl;
$R_{15}$ is selected from hydrogen, and alkyl; and
$R_{19}$ is selected from alkyl, and aryl;
where alkyl is unsubstituted or substituted by one or two of the same or different groups selected from: hydroxy, halogen, amino, hydroxyalkyl, alkoxy, aryl, aryloxy, and heterocyclyl;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, and alkoxy;
heterocyclyl is unsubstituted or substituted by one or two of the same or different groups selected from: halogen, hydroxy, amino, alkyl, hydroxyalkyl, and alkoxy.

In one embodiment, the present invention provides compounds represented by formula (1), wherein,
$R_1$ is halogen;
$R_2$ is hydrogen;
$R_3$ is alkyl;
$R_4$ is formula (4):

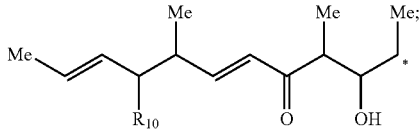

* indicates point of attachment
$R_{10}$ is halogen;
where alkyl is unsubstituted or substituted by one or two of the same or different groups selected from: hydroxy, halogen, amino, hydroxyalkyl, and alkoxy.

In one embodiment, the present invention provides compounds represented by formula (1), wherein, $R_1$ is absent and $R_2$ is =O;
$R_3$ is alkyl;
$R_4$ is formula (4):

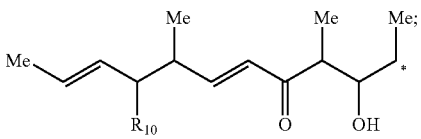

* indicates point of attachment
$R_{10}$ is selected from halogen, hydroxy, alkoxy, —$SR_{14}$, —$NR_{14}R_{15}$, and —$O(CO)R_{19}$;
$R_{14}$ is selected from hydrogen, alkyl, aralkyl, aryl, and heterocyclyl;
$R_{15}$ is selected from hydrogen, and alkyl; and
$R_{19}$ is selected from alkyl, aryl, aralkyl, and heterocyclyl;
where alkyl is unsubstituted or substituted by one or two of the same or different groups selected from: hydroxy, halogen, amino, hydroxyalkyl, and alkoxy;
alkoxy is unsubstituted or substituted by one or two of the same or different groups selected from: halogen, hydroxy, alkyl, and hydroxyalkyl;
aryl is unsubstituted or substituted by one or two of the same or different groups selected from: halogen, hydroxy, amino, alkyl, hydroxyalkyl, and alkoxy;
heterocyclyl is unsubstituted or substituted by one or two of the same or different groups selected from: halogen, hydroxy, amino, alkyl, hydroxyalkyl, and alkoxy.

In one embodiment, the present invention provides compounds represented by formula (1), wherein,
$R_1$ is absent and $R_2$ is =O;
$R_3$ is methyl;
$R_4$ is formula (4):

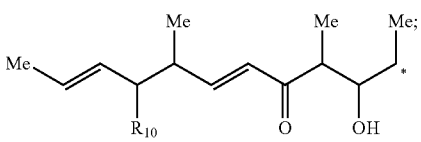

* indicates point of attachment
$R_{10}$ is selected from hydroxy, and alkoxy.

In one embodiment, the present invention provides compounds represented by formula (1), wherein
$R_1$ is absent and $R_2$ is =O;
$R_3$ is alkyl; and
$R_4$ is formula (5):

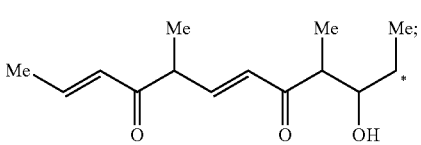

* indicates point of attachment
In one embodiment, the present invention provides compounds represented by formula (1) wherein,
$R_1$ is selected from halogen, hydroxy, and alkoxy;
$R_2$ is hydrogen;
$R_3$ is alkyl;

$R_4$ is formula (8):

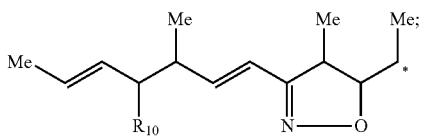

* indicates point of attachment
$R_{10}$ is selected from halogen, and hydroxy;
where alkyl is unsubstituted or substituted by one or two of the same or different groups selected from: hydroxy, halogen, amino, hydroxyalkyl, alkoxy, aryl, aryloxy, and heterocyclyl; alkoxy is unsubstituted or substituted by one or two of the same or different groups selected from: halogen, hydroxy, alkyl, and hydroxyalkyl.

In one embodiment, the present invention provides compounds represented by formula (1), wherein,
$R_1$ is selected from hydroxy, and alkoxy;
$R_2$ is hydrogen;
$R_3$ is methyl;
$R_4$ is formula (8):

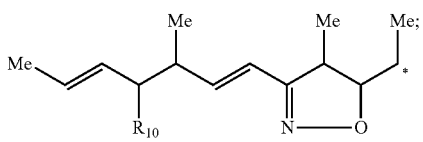

* indicates point of attachment
$R_{10}$ is hydroxy.

In one embodiment, the present invention provides compounds represented by formula (1), wherein,
$R_1$ is selected from halogen, hydroxy, and alkoxy;
$R_2$ is hydrogen;
$R_3$ is alkyl; and
$R_4$ is formula (9):

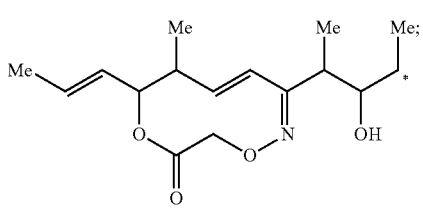

* indicates point of attachment
where alkyl is unsubstituted or substituted by one or two of the same or different groups selected from: hydroxy, halogen, amino, hydroxyalkyl, alkoxy, aryl, aryloxy, and heterocyclyl; alkoxy is unsubstituted or substituted by one or two of the same or different groups selected from: halogen, hydroxy, alkyl, and hydroxyalkyl.

Compounds of the present invention are selected from but not limited to:

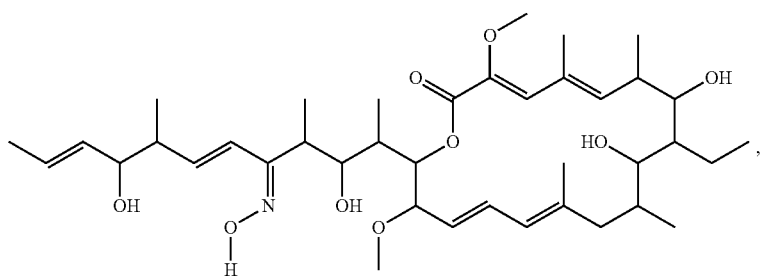

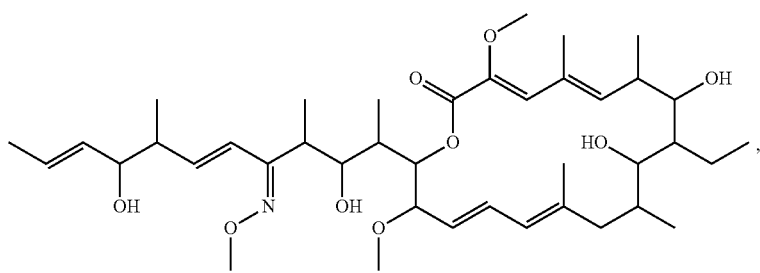

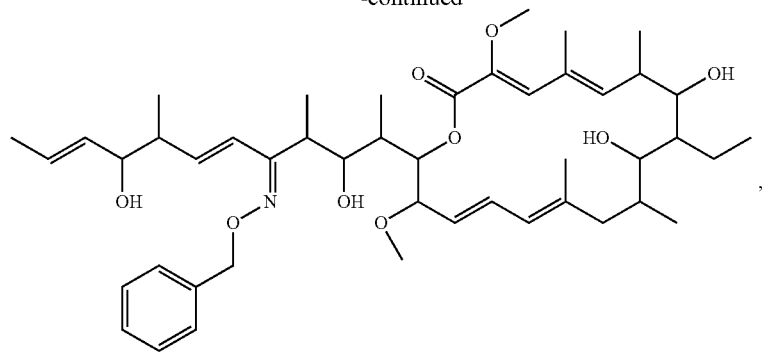,
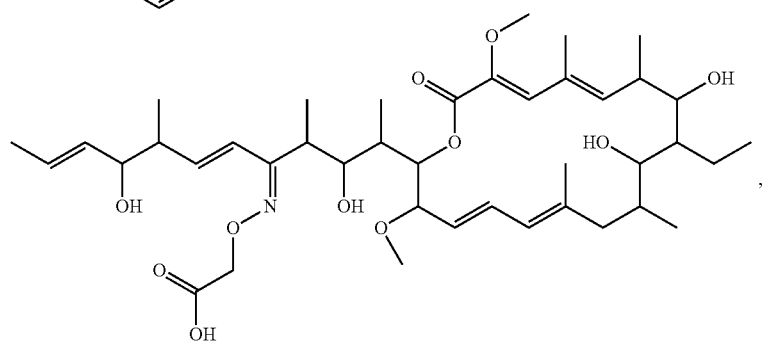,
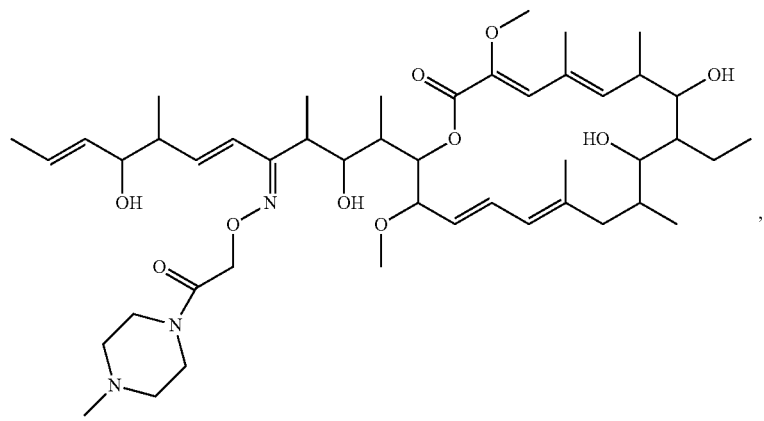,
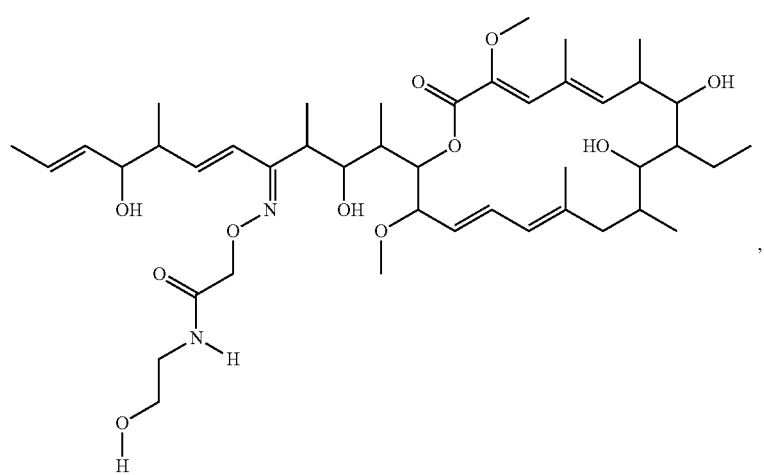,

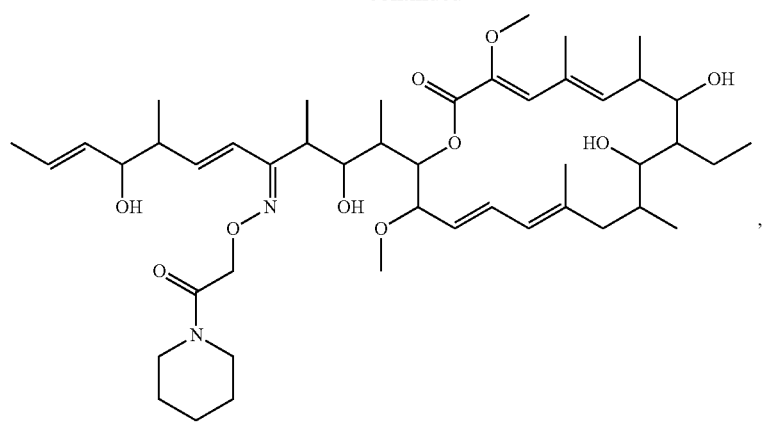,
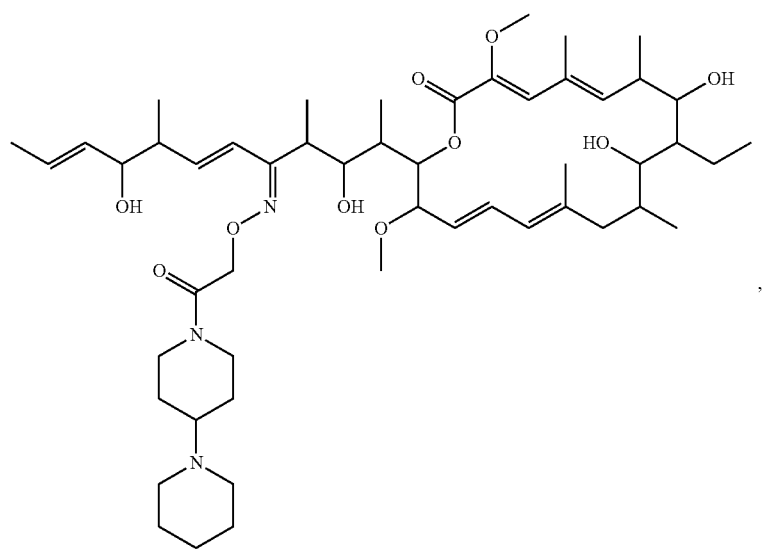,
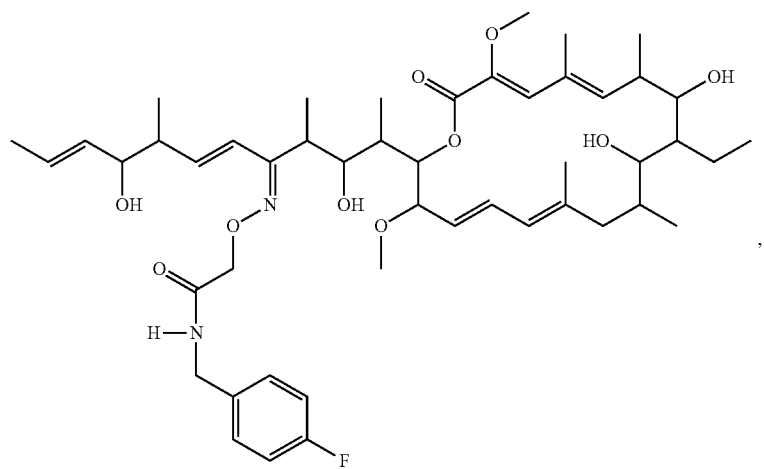,
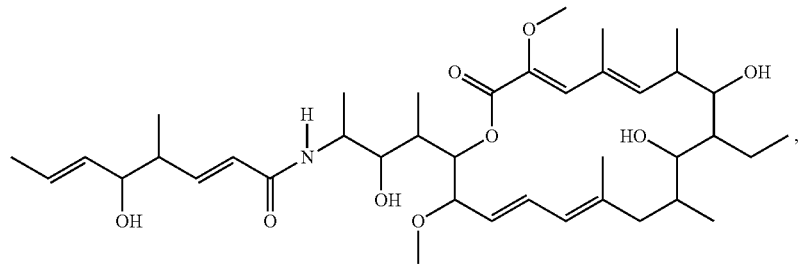,

-continued

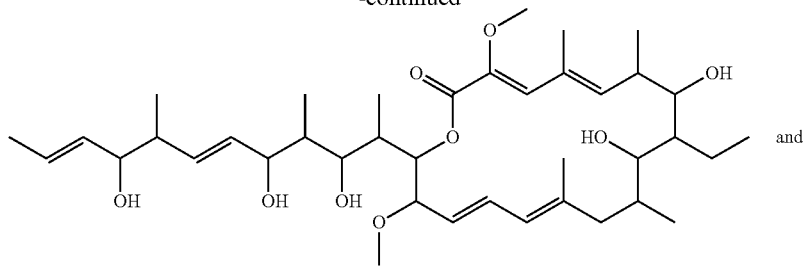

and their stereoisomeric and tautomeric forms, pharmaceutically acceptable salts, solvates and prodrugs.

DETAILED DESCRIPTION OF THE SCHEMES

The compounds of the present invention also include all stereoisomeric forms and mixtures thereof and their pharmaceutically acceptable salts, solvates and polymorphs. Furthermore, all prodrugs and derivatives of the compounds are a subject of the present invention.

According to another aspect of present invention, the compounds of formula (1) can be prepared in a number of ways including using methods well known to the person skilled in the art. Examples of methods to prepare the present compounds are described below and illustrated in Schemes 1 to 4 but are not limited thereto. It will be appreciated by persons skilled in the art that the processes described herein, the order of the synthetic steps employed may be varied and will depend inter alia on factors such as the nature of functional groups present in a particular substrate and the protecting group strategy (if any) to be adopted and will also influence the choice of reagent to be used in the synthetic steps.

The reagents, reactants and intermediates used in the following processes are either isolated from fermentation of microorganisms, are commercially available or can be prepared according to standard literature procedures known in the art or a combination thereof. The starting compounds and the intermediates used for the synthesis of compounds of the present invention, are referred to with general symbols namely (A), (B), (C), (D), (E), (F), (G), (H), (K), (L), (M), (N), (O), (O), (R), (S), (T), and (U). Throughout the process description, the corresponding substituent groups in the various formulae representing starting compounds and intermediates have the same meanings as that for the compounds of formula (1) as described in detailed description.

The processes used in various schemes of the present invention, are referred to with general symbols namely 1a, 1b, 1c, 1d, 1e, 1f, 1g, 2a, 2b, 2c, 2d, 3a, 3b, 3c, 4a, 4b, 4c, and 4d. Processes for the preparation of compounds of the present invention are set forth in the following schemes:

Scheme 1

Concanamycin crude (in Scheme 1) is obtained by fermentation of a culture (PM0224355). The whole broth is extracted using a solvent selected from ethyl acetate, chloroform and dichloromethane. Concanamycin crude is isolated by column chromatography and is characterized by spectral comparison (The Journal of Antibiotics, Vol. 45, No. 7, 1108-1116, (1992)).

Step 1a

Concanamycin crude (in Scheme 1) is subjected to alkaline hydrolysis as per procedure described in reference (Tetrahedron Letters, Vol. 22, No. 39, 3857-60, (1981)), to obtain the compound of formula (1) (wherein $R_1$ is hydroxy, $R_2$ is hydrogen, $R_3$ is methyl, $R_4$ is formula (4), and $R_{10}$ is hydroxy; denoted as formula (A) in Scheme 1).

Step 1b

Compound of formula (1) (wherein $R_1$ is hydroxy, $R_2$ is hydrogen, $R_3$ is methyl, $R_4$ is formula (3), $R_8$ is hydroxy, and $R_9$ is hydroxy; denoted as formula (B) in Scheme 1) is prepared by reacting compound of formula (A) (wherein $R_1$ is hydroxy, $R_2$ is hydrogen, $R_3$ is methyl, $R_4$ is formula (4), and $R_{10}$ is hydroxy) with an amine hydrochloride such as hydroxylamine hydrochloride in presence of a base selected from pyridine, substituted pyridine, triethylamine, diisopropylethylamine, N-methylmorpholine, and N-ethylmorpholine using a solvent selected from methanol, ethanol, propanol, butanol, tetrahydrofuran, dimethylformamide, 1,4-dioxane, and acetonitrile. The reaction mixture is stirred at a temperature in the range of 0° C. to 45° C. in an inert atmosphere such as nitrogen gas, over a time period ranging from 4 h to 16 h.

Step 1c

Compound of formula (1) (wherein $R_1$ is hydroxy, $R_2$ is hydrogen, $R_3$ is methyl, $R_4$ is formula (6), and $R_{10}$ is hydroxy; denoted as formula (C) in Scheme 1) is prepared by reacting compound of formula (B) (wherein $R_1$ is hydroxy, $R_2$ is hydrogen, $R_3$ is methyl, $R_4$ is formula (3), $R_8$ is hydroxy, and $R_9$ is hydroxy) in a solvent selected from acetone, acetonitrile, and 1,4-dioxane with tosyl chloride or 2,4,6-trichloro-1,3,5-triazine (TCT), in presence of a base selected from sodium hydroxide and potassium hydroxide, in an inert atmosphere such as nitrogen at 0° C., for 2 h. The reaction mixture can be further stirred at a temperature in the range of 25° C. to 45° C., in an inert atmosphere such as nitrogen gas, over a time period ranging from 2 h to 8 h.

Step 1d

Compound of formula (1) (wherein $R_1$ is hydroxy, $R_2$ is hydrogen, $R_3$ is methyl, $R_4$ is formula (3), $R_8$ is hydroxy, and $R_9$ is methoxy or benzyloxy; denoted as formula (D) in Scheme 1) is prepared by reacting compound of formula (A) (wherein $R_1$ is hydroxy, $R_2$ is hydrogen, $R_3$ is methyl, $R_4$ is formula (4), and $R_{10}$ is hydroxy) with an amine hydrochloride selected from methoxyamine hydrochloride, and benzyloxy amine hydrochloride in presence of a base selected from pyridine, substituted pyridine, triethylamine, diisopropylethylamine, N-methylmorpholine, and N-ethylmorpholine using a solvent selected from methanol, ethanol, propanol, butanol, tetrahydrofuran, dimethylformamide, dioxane, and acetonitrile. The reaction mixture is stirred at a temperature in the range of 0° C. to 45° C., in an inert atmosphere such as nitrogen gas, over a time period ranging from 4 h to 16 h.

Step 1e

Compound of formula (1) (wherein $R_1$ is hydroxy, $R_2$ is hydrogen and $R_3$ is methyl, $R_4$ is formula (3), $R_8$ is hydroxy, $R_9$ is —OCH$_2$COOR$_{17}$, and $R_{17}$ is hydrogen; denoted as formula (E) in Scheme 1) is prepared by reacting compound of formula (A) (wherein $R_1$ is hydroxy, $R_2$ is hydrogen, $R_3$ is methyl, $R_4$ is formula (4), and $R_{10}$ is hydroxy) with amine hydrochloride such as carboxymethylhydroxylamine hemi hydrochloride in presence of a base selected from pyridine, substituted pyridine, triethylamine, diisopropylethylamine, N-methylmorpholine and N-ethylmorpholine using a solvent selected from methanol, ethanol, propanol, butanol, tetrahydrofuran, dimethylformamide, 1,4-dioxane, and acetonitrile. The reaction mixture is stirred at a temperature in the range of 0° C. to 45° C., in an inert atmosphere such as nitrogen gas, over a time period ranging from 4 h to 16 h.

Step 1f

Compound of formula (1) (wherein $R_1$ is hydroxy, $R_2$ is hydrogen, $R_3$ is methyl, $R_4$ is formula (3), $R_8$ is hydroxy, $R_9$ is —OCH$_2$COR$_{18}$, $R_{18}$ is selected from heterocyclyl and —NHCH$_2$R$_{20}$, and $R_{20}$ is selected from alkyl, and aryl; denoted as formula (F) in Scheme 1) is prepared by dissolving compound of formula (E) (wherein $R_1$ is hydroxy, $R_2$ is hydrogen, $R_3$ is methyl, $R_4$ is formula (3), $R_8$ is hydroxy, $R_9$ is —OCH$_2$COOR$_{17}$, and $R_{17}$ is hydrogen) in a solvent selected from dichloromethane, acetonitrile, chloroform, ethyl acetate, and dimethylformamide, and reacting with a coupling reagent selected from dicyclohexylcarbodiimide, 1-ethyl-3-(3-dimethyllaminopropyl)carbodiimide hydrochloride (EDC HCl), N,N'-diisopropyl carbodiimide (DIC), or O-benzotriazol-1-yl-N,N,N',N'-tetramethyl uranium hexa fluorophosphate (HBTU), O-benzotriazol-1-yl-N,N,N',N'-tetramethyluroniumtetrafluoroborate (TBTU), benzotriazol-1-yl-oxytripyrrolidinophosphonium hexafluorophosphate (PyBOP) and N-hydroxy benzotriazole (HOBt). Further, the reaction mixture is treated with an amine such as N-methylpiperazine, ethanolamine, piperidine, 4-piperidines-piperidine, and 4-fluoro phenylamine. The reaction mixture is stirred at a temperature in the range of 25° C. to 45° C., in an inert atmosphere such as nitrogen gas, over a time period ranging from 4 h to 18 h.

Step 1g

Compound of formula (1) (wherein $R_1$ is hydroxy, $R_2$ is hydrogen, $R_3$ is methyl, $R_4$ is formula (7), $R_{10}$ is hydroxy, $R_{11}$ is hydrogen, and $R_{12}$ is hydroxy; denoted as formula (G) in Scheme 1) is prepared by dissolving compound of formula (A) (wherein $R_1$ is hydroxy, $R_2$ is hydrogen, $R_3$ is methyl, $R_4$ is formula (4), and $R_{10}$ is hydroxy) in a solvent selected from tetrahydrofuran, acetonitrile, acetone, methanol and ethanol, and is reacted with a reducing agent such as sodium borohydride, in an inert atmosphere such as nitrogen at 0° C. for 20 min The reaction mixture is further stirred at a temperature in the range of 25° C. to 45° C., in an inert atmosphere such as nitrogen gas, over a time period ranging from 2 h to 8 h.

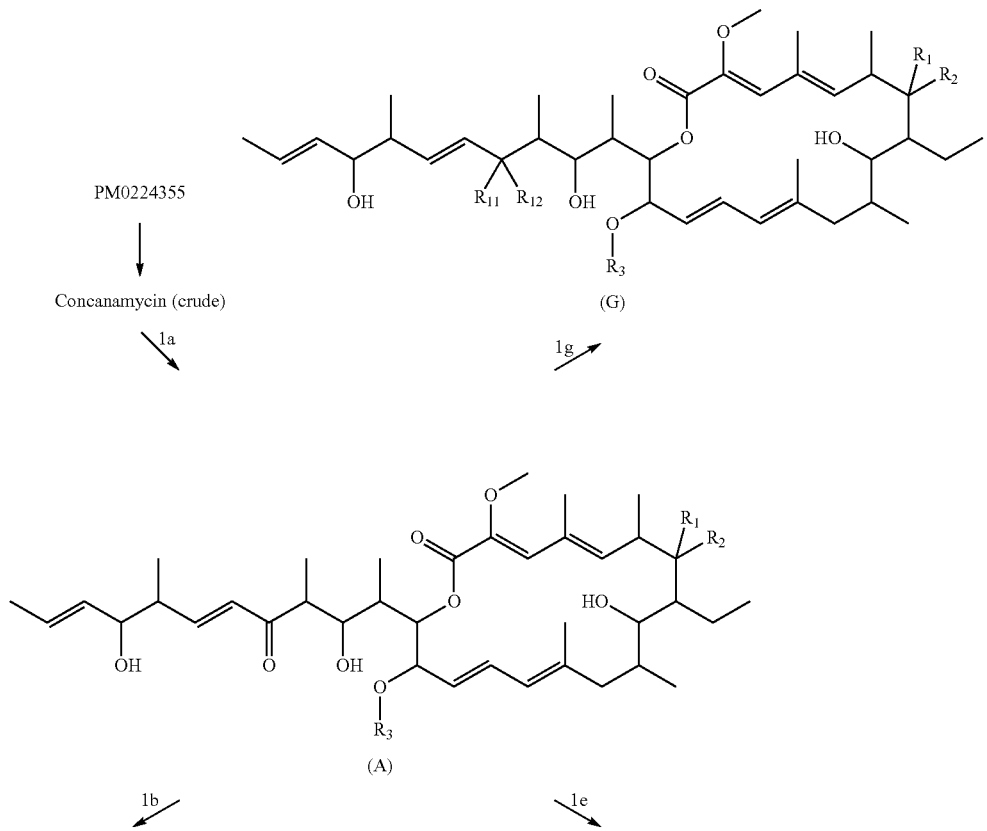

Scheme 1

29

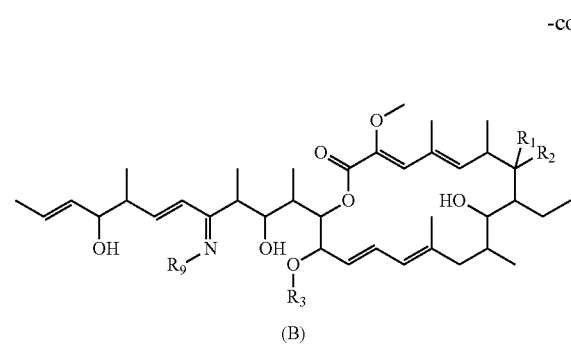

(B)

1c ↓

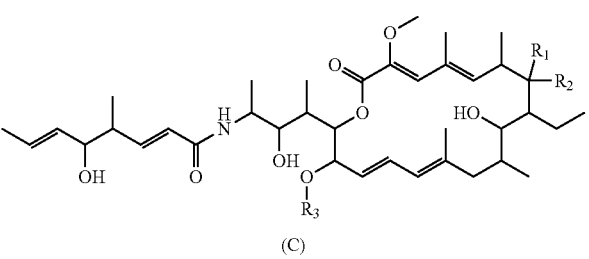

(C)

-continued

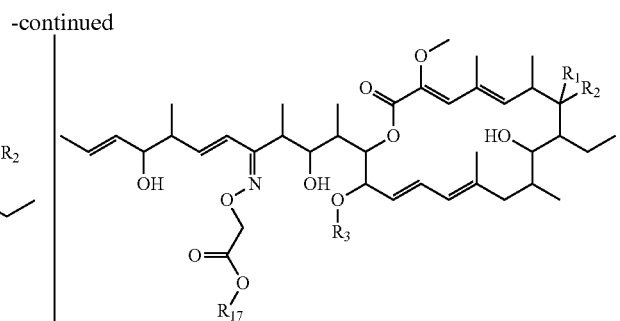

(E)

1d

1f ↓

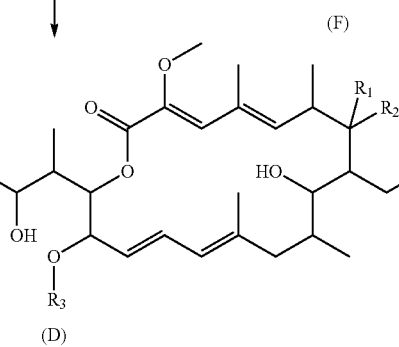

(F)

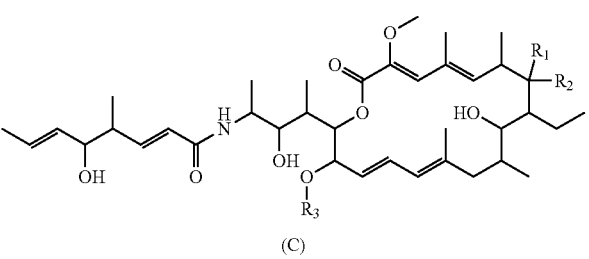

(D)

Scheme 2

Step 2a

Compound of formula (1) (wherein $R_1$ is hydroxy, $R_2$ is hydrogen, $R_3$ is methyl, $R_4$ is formula (8), and $R_{10}$ is hydroxy; denoted as formula (H), in Scheme 2) is prepared by dissolving compound of formula (B) (wherein $R_1$ is hydroxy, $R_2$ is hydrogen, $R_3$ is methyl; $R_4$ is formula (3), $R_8$ is hydroxy, and $R_9$ is hydroxy; prepared by step 1b, Scheme 1) in a solvent selected from acetone, acetonitrile, 1,4-dioxane, with reagent such as tosyl chloride, in presence of a base selected from sodium hydroxide and potassium hydroxide, in an inert atmosphere such as nitrogen at 0° C., for 2 h. The reaction mixture can be further stirred at a temperature in the range of 25° C. to 45° C., in an inert atmosphere such as nitrogen gas, over a time period ranging from 2 h to 8 h.

Step 2b

Compound of formula (1) (wherein $R_1$ is hydroxy, $R_2$ is hydrogen, $R_3$ is methyl; and $R_4$ is formula (9); denoted as formula (K) in Scheme 2 is prepared by dissolving compound of formula (E) (wherein $R_1$ is hydroxy, $R_2$ is hydrogen, $R_3$ is methyl, $R_4$ is formula (3), $R_8$ is hydroxy and $R_9$ is —OCH$_2$COOR$_{17}$, $R_{17}$ is hydrogen; prepared by step 1e, Scheme 1)) in a solvent selected from dichloromethane, acetonitrile, chloroform, ethyl acetate, and dimethylformamide, and reacting with coupling reagent selected from dicyclo hexylcarbodiimide, 1-ethyl-3-(3-dimethylaminopropyl) carbodiimide hydrochloride (EDC HCl) and N,N'-diisopropyl carbodiimide (DIC) and catalyst such as 4-dimethylaminopyridine (DMAP). The reaction mixture is stirred at a temperature in the range of 25° C. to 45° C., in an inert atmosphere such as nitrogen gas, over a time period ranging from 4 h to 18 h.

Step 2c

Compound of formula (1) (wherein $R_1$ is absent, $R_2$ is =O, $R_3$ is methyl, and $R_4$ is formula (4), and $R_{10}$ is hydroxy; denoted as formula (L), in Scheme 2) is prepared by reacting compound of formula (A) (wherein $R_1$ is hydroxy, $R_2$ is hydrogen, $R_3$ is methyl, $R_4$ is formula (4), and $R_{10}$ is hydroxy) in a solvent selected from dichloromethane, diethyl ether, and tetrahydrofuran with an oxidizing agent selected from Dess-martin periodinane, pyridinium dichromate, pyridinium chlorochromate, and Swern oxidizing agent in an inert atmosphere such as nitrogen at 0° C. for 2 h. The reaction mixture is further stirred at a temperature in the range of 25° C. to 45° C., under inert atmosphere such as nitrogen gas, over a time period ranging from 2 h to 8 h.

Step 2d

Compound of formula (1) (wherein $R_1$ is absent, $R_2$ is =O, $R_3$ is methyl, and $R_4$ is formula (5); denoted as formula (M), in Scheme 2) is prepared by reacting compound of formula (A) (wherein $R_1$ is hydroxy, $R_2$ is hydrogen, $R_3$ is methyl, $R_4$ is formula (4) and $R_{10}$ is hydroxy) in a solvent selected from dichloromethane, diethyl ether, and tetrahydrofuran with an oxidizing agent selected from Dess-martin periodinane, pyridinium dichromate, pyridinium chlorochromate, and Swern oxidizing agent in an inert atmosphere such as nitrogen at 0° C. for 2 h. The reaction mixture is further stirred at a temperature in the range of 25° C. to 45° C., under inert atmosphere such as nitrogen gas, over a time period ranging from 2 h to 8 h.

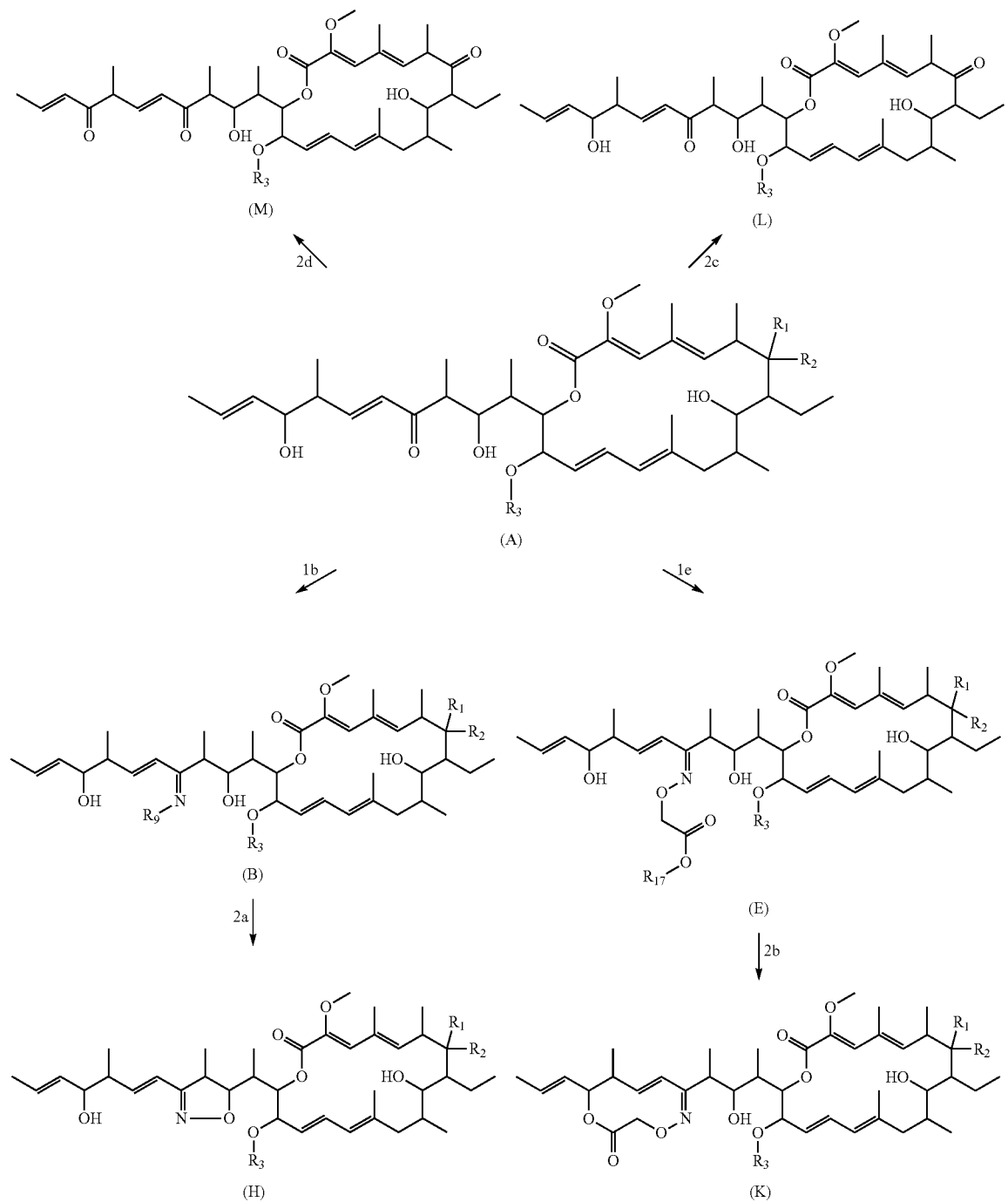

Scheme 2

Scheme 3

Step 3a

Compound of formula (1) (wherein $R_1$ is hydroxy, $R_2$ is hydrogen, $R_3$ is methyl, $R_4$ is formula (4), and $R_{10}$ is —OC(O)$R_{19}$, $R_{19}$ is selected from alkyl, aralkyl, aryl, and heterocyclyl; denoted as formula (N), in Scheme 3) is prepared by dissolving compound of formula (A) (wherein $R_1$ is hydroxy, $R_2$ is hydrogen, $R_3$ is methyl, $R_4$ is formula (4) and $R_{10}$ is hydroxy) in a solvent selected from dichloromethane, acetonitrile, chloroform, ethyl acetate, and dimethylformamide, and reacting with a coupling reagent selected from dicyclohexylcarbodiimide or EDC HCl or DIC in presence of a catalyst such as DMAP. Further, the reaction mixture is treated with $R_{19}$—COOH ($R_{19}$ is selected from alkyl, aralkyl, aryl, and heterocyclyl) is added to the reaction mixture and at a temperature in the range of 25° C. to 45° C., in an inert atmosphere such as nitrogen gas, over a time period ranging from 4 h to 18 h.

Step 3b

Compound of formula (1) (wherein $R_1$ is hydroxy, $R_2$ is hydrogen, $R_3$ is selected from ethyl, n-propyl, n-butyl and n-pentyl; $R_4$ is formula (4), and $R_{10}$ is hydroxy; denoted as formula (O), in Scheme 3) is prepared by dissolving a compound of formula (A) (wherein $R_1$ is hydroxy, $R_2$ is hydrogen, $R_3$ is methyl, $R_4$ is formula (3), and $R_{10}$ is hydroxy), in a solvent selected from dichloromethane, acetonitrile, chloroform, ethyl acetate, and dimethylformamide, and reacting with $R_3$—OH (wherein $R_3$ is selected from ethyl, n-propyl, n-butyl and n-pentyl) in presence of para-toluene sulphonic acid. The reaction mixture is stirred at a temperature in the range of 25° C. to 45° C., under inert atmosphere such as nitrogen gas, over a time period ranging from 4 h to 18 h.

Step 3c

Compound of formula (1) (wherein $R_1$ is hydroxy, $R_2$ is hydrogen, $R_3$ is methyl, $R_4$ is formula (2), $R_5$ is hydroxy, $R_6$ is hydrogen, and $R_7$ is selected from hydrogen or alkyl; denoted as formula (O), in Scheme 3) is prepared by dissolving a compound of formula (B) (wherein $R_1$ is hydroxy, $R_2$ is hydrogen, $R_3$ is methyl, $R_4$ is formula (3), $R_8$ is hydroxy and $R_9$ is hydroxy; prepared by step 1b, Scheme 1) in a solvent selected from dichloromethane, acetonitrile, chloroform, ethyl acetate, and dimethylformamide, and is reacted with $R_7$-halide (wherein $R_7$ is hydrogen or alkyl) in presence of a base selected from triethylamine, diisopropylethylamine, N-methylmorpholine, and N-ethylmorpholine. The reaction mixture is stirred at a temperature in the range of 25° C. to 45° C., in an inert atmosphere such as nitrogen gas, over a time period ranging from 4 h to 18 h.

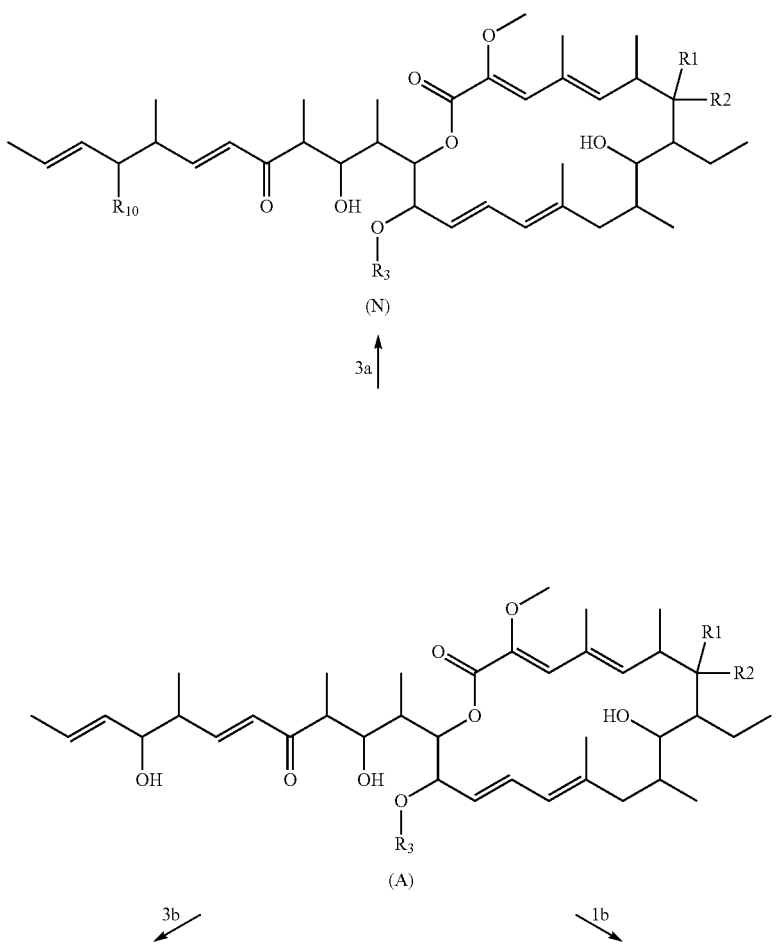

Scheme 3

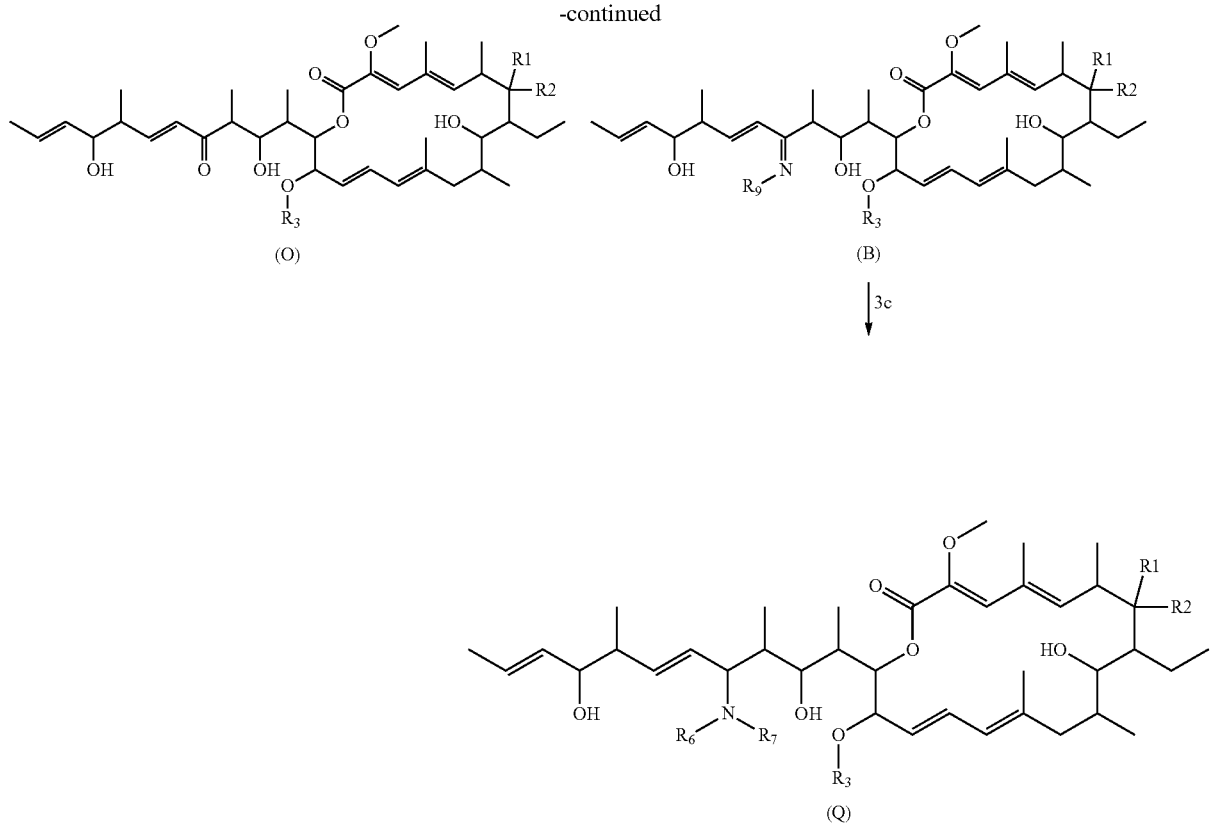

Scheme 4

Step 4a

Compound of formula (1) (wherein $R_1$ is hydroxy, $R_2$ is hydrogen, $R_3$ is methyl, $R_4$ is formula (7), $R_{10}$ is hydroxy, $R_{11}$ is halogen and $R_{12}$ is halogen; denoted as formula (R), in Scheme 4) is prepared by reacting compound of formula (A) (wherein $R_1$ is hydroxy, $R_2$ is hydrogen, $R_3$ is alkyl, $R_4$ is formula (4), and $R_{10}$ is hydroxy) with an halogenating agent such as diethylaminosulfur trifluoride (DAST) in a solvent selected from tetrahydrofuran, dimethylformamide, 1,4-dioxane and acetonitrile at a temperature in the range of 0° C. to 45° C., in an inert atmosphere such as nitrogen gas, over a time period ranging from 2 h to 8 h.

Step 4b

Compound of formula (1) (wherein $R_1$ is halogen, $R_2$ is hydrogen, $R_3$ is methyl, $R_4$ is formula (4), and $R_{10}$ is halogen; denoted as formula (S), in Scheme 4) is prepared by reacting compound of formula (A) (wherein $R_1$ is hydroxy, $R_2$ is hydrogen, $R_3$ is methyl, $R_4$ is formula (4), and $R_{10}$ is hydroxy) with an halogenating agent such as diethylaminosulfur trifluoride (DAST) in a solvent selected from tetrahydrofuran, dimethylformamide, 1,4-dioxane and acetonitrile at a temperature in the range of 0° C. to 45° C., in an inert atmosphere such as nitrogen gas, over a time period ranging from 2 h to 8 h.

Step 4c

Compound of formula (1) (wherein $R_1$ is amino, $R_2$ is hydrogen, $R_3$ is methyl, $R_4$ is formula (4), $R_{10}$ is —$NR_{14}R_{15}$, $R_{14}$ is selected from alkyl, aralkyl, aryl and heterocyclyl and $R_{15}$ is selected from hydrogen and alkyl; denoted as formula (T), in Scheme 4) is prepared by reacting compound of formula (A) (wherein $R_1$ is hydroxy, $R_2$ is hydrogen, $R_3$ is methyl, $R_4$ is formula (4), and $R_{10}$ is hydroxy) with sodium triacetoxyborohydride or sodium cyanoborohydride and amine selected from $R_{14}$—$NH_2$ and $R_{14}$—NH-alkyl (wherein $R_{14}$ is selected from alkyl, aralkyl, aryl, and heterocyclyl) in a solvent selected from benzene, toluene, tetrahydrofuran, dimethylformamide, 1,4-dioxane and acetonitrile at a temperature in the range of 0° C. to 45° C., in an inert atmosphere such as nitrogen gas, over a time period ranging from 2 h to 8 h.

Step 4d

Compound of formula (1) (wherein $R_1$ is SH, $R_2$ is hydrogen, $R_3$ is methyl, $R_4$ is formula (4), and $R_{10}$ is —$SR_{14}$, $R_{14}$ is selected from alkyl, aralkyl, aryl and heterocyclyl; denoted as formula (U), in Scheme 4) is prepared by reacting compound of formula (A) (wherein $R_1$ is hydroxy, $R_2$ is hydrogen, $R_3$ is methyl, $R_4$ is formula (4), and $R_{10}$ is hydroxy) with a reducing agent selected from sodium triacetoxyborohydride and sodium cyanoborohydride and $R_{14}$—SH (wherein $R_{14}$ is selected from alkyl, aralkyl, aryl and heterocyclyl) in presence of a solvent selected from solvent benzene or toluene, tetrahydrofuran, dimethylformamide, 1,4-dioxane and acetonitrile at a temperature in the range of 0° C. to 45° C., in an inert atmosphere such as nitrogen gas, over a time period ranging from 2 h to 8 h.

Scheme 4

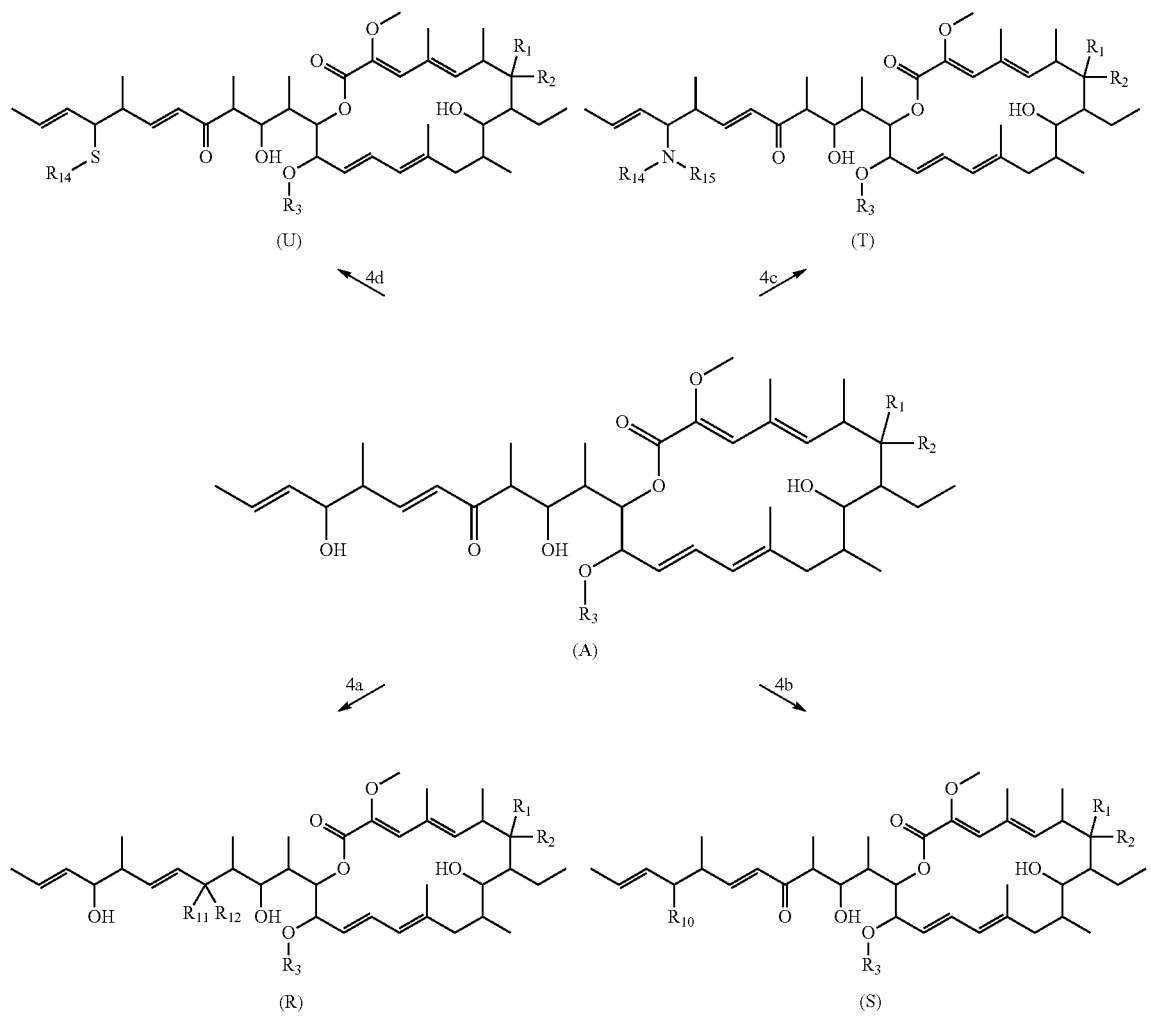

In all the above mentioned schemes 1 to 4, wherever applicable the compounds may be optionally converted into their prodrugs and salts. Additionally the compounds can be separated into individual isomers by techniques well known in the art such as column chromatography.

It will be appreciated by those skilled in the art that the compounds of the present invention can also be utilized in the form of their pharmaceutically acceptable salts or solvates thereof. With respect to the compounds of formula (1) the present invention also includes all stereoisomeric forms and mixtures thereof in all ratios and their pharmaceutically acceptable salts.

The compounds of the present invention can subsequently be converted into their organic or inorganic salts.

Thus, when the compounds of the present invention represented by the formula (1) contain one or more basic groups, i.e. groups which can be protonated, they can form an addition salt with a suitable inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art.

The compounds of the present invention represented by the formula (1) contain one or more acidic group they can form an addition salt with a suitable base. For example, such salts of the compounds of the present invention may include their alkali metal salts such as Li, Na, and K salts, or alkaline earth metal salts like Ca, Mg salts, or aluminium salts, or salts with ammonia or salts of organic bases such as lysine, arginine, guanidine, diethanolamine, choline, and tromethamine.

The present invention furthermore includes solvates of the compounds of formula (1), for example hydrates with water and the solvates formed with other solvents of crystallization, such as alcohols, ethers, ethyl acetate, dioxane, dimethylformamide or a lower alkyl ketone such as acetone, or mixtures thereof.

The present invention furthermore includes polymorphs of the compounds of formula (1). Polymorphs may be obtained by heating or melting the compounds of present invention followed by gradual or fast cooling. The presence of polymorphs may be determined by techniques such as IR spectroscopy, solid probe NMR spectroscopy, differential scanning calorimetry, or powder X-ray diffraction.

The present invention also includes prodrugs of the compounds of formula (1), for example esters, amides and other derivatives.

The expression "prodrug" refers to compounds that are drug precursors, which following administration, release the drug in vivo via a chemical or physiological process e.g., a prodrug on being brought to the physiological pH or through an enzyme action is converted to the desired drug form.

The compounds of the present invention find use in the treatment of cancers. Compounds are used to reduce, inhibit, or diminish the proliferation of tumor cells, and thereby assist in reducing the size of a tumor. Representative cancers that may be treated by such compounds include but are not limited to bladder cancer, breast cancer, colorectal cancer, endometrial cancer, gastric cancer, head & neck cancer, kidney cancer, melanoma, non-small-cell lung cancer, ovarian cancer, pancreatic cancer, prostate cancer, renal cancer, soft tissue sarcoma, as well as esophageal cancer, cervical cancer of uterus, testicular and germ cell cancer, thyroid cancer, brain tumors (glioblastoma, cerebellar astrocytoma, cerebral astrocytoma, ependymoma, medulloblastoma, neuroblastoma, retinoblastoma, supratentorial primitive neuroectodermal and pineal tumors, visual pathway and hypothalamic glioma, brain stem glioma), liver cancer, Ewing's sarcoma family of tumors, osteosarcoma, malignant fibrous histiocytoma of bone, rhabdomyosarcoma, skin cancer, small-cell lung cancer, Wilms' tumors, leukemias (acute lymphoblastic leukemia, adult acute myeloid leukemia, chronic lymphocytic leukemia, chronic myeloid leukemia), and lymphomas (Hodgkin's disease, non-Hodgkin's lymphoma, hairy cell leukemia, multiple myeloma, primary central nervous system lymphoma), among others.

According to an embodiment, representative cancers that may be treated by compounds of the present invention include bladder cancer, breast cancer, colorectal cancer, endometrial cancer, gastric cancer, head & neck cancer, kidney cancer, melanoma, non-small-cell lung cancer, ovarian cancer, pancreatic cancer, prostate cancer, renal cancer, soft tissue sarcoma, esophageal cancer, cervical cancer of uterus, testicular cancer, thyroid cancer, medulloblastoma, neuroblastoma, supratentorial primitive neuroectodermal and pineal tumors, brain stem glioma, liver cancer, osteosarcoma, small-cell lung cancer, acute lymphoblastic leukemia, adult acute myeloid leukemia, chronic lymphocytic leukemia, chronic myeloid leukemia, Hodgkin's disease, non-Hodgkin's lymphoma, hairy cell leukemia, and multiple myeloma.

According to another embodiment, representative cancers that may be treated by compounds of the present invention include bladder cancer, breast cancer, colorectal cancer, melanoma, non-small-cell lung cancer, small-cell lung cancer, and prostate cancer.

Additional compound useful in the treatment of cancer in accordance with the present invention includes compound of formula 1 wherein $R_1$ is hydroxy, $R_2$ is hydrogen, $R_3$ is methyl, $R_4$ is formula (4):

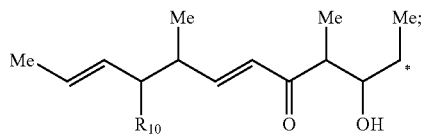

* indicates point of attachment
and $R_{10}$ is hydroxy; and is referred herein as formula (1a):

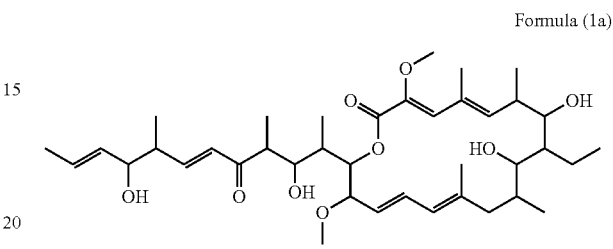

Formula (1a)

The term "subject" as used herein refers to an animal, preferably a mammal, and most preferably a human.

The term "mammal" used herein refers to warm-blooded vertebrate animals of the class Mammalia, including humans, characterized by a covering of hair on the skin and, in the female, milk-producing mammary glands for nourishing the young. The term mammal includes animals such as cat, dog, rabbit, bear, fox, wolf, monkey, deer, mouse, pig as well as human.

According to an embodiment, the present invention provides a method for the treatment of cancer by administering to a mammal in need thereof a therapeutically effective amount of a compound of formula (1) or compound of formula (1a).

According to another aspect of the present invention, there are provided pharmaceutical compositions including therapeutically effective amount of one or more compounds of formula (1) or compound of formula (1a) as active ingredient and pharmaceutically acceptable carrier, useful in the treatment of cancer.

The term 'treating", "treat" or "treatment" as used herein refers to alleviate, slow the progression, attenuation or cure of existing disease (for example, cancer).

By "pharmaceutically acceptable" is meant that the carrier, diluent, excipients, and/or salt must be compatible with the other ingredients of the formulation, and not deleterious to the recipient thereof.

The term "pharmaceutically acceptable carrier" as used herein means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The term, "therapeutically effective amount" as used herein means an amount of compound or composition (e.g. compound of formula (1)) sufficient to significantly induce a positive modification in the condition to be regulated or treated, but low enough to avoid undue or severe side effects within the scope of sound medical judgment. The therapeutically effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors. As used herein, all percentages are by weight unless otherwise specified.

According to another aspect of present invention, there are provided methods of treatment of cancer using these compositions as described herein above.

According to another aspect of present invention there is provided the use of one or more compounds of formula (1) or compound of formula (1a) for the treatment of cancer.

According to another aspect of present invention there are provided methods for manufacture of medicaments including one or more compounds of formula (1) or compound of formula (1a), which are useful for the treatment of cancer.

The pharmaceutical compositions according to the present invention are prepared in a manner known per se and familiar to one skilled in the art. Pharmaceutically acceptable inert inorganic and/or organic carriers and/or additives can be used in addition to the compound(s) of the formula (1) or compound of formula (1a), and/or its salts and/or its prodrugs. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

In addition to the active ingredients of the compound of formula (1) or compound of formula (1a), and/or its salts and/or prodrugs and carrier substances, the pharmaceutical compositions can contain additives such as, for example, fillers, antioxidants, dispersants, emulsifiers, defoamers, flavors, preservatives, solubilizers or colorants. The pharmaceutical compositions of the present invention can also contain one or more compounds of the formula (1) or compound of formula (1a) and/or its salts and/or their prodrugs. Furthermore, in addition to at least one compound of the formula (1) or compound of formula (1a), and/or its prodrugs, the pharmaceutical compositions can also contain one or more other therapeutically or prophylactically active ingredients.

The pharmaceutical compositions normally contain about 1 to 99%, for example, about 5 to 70%, or about 10 to about 30% by weight of the compounds of formula (1) or compound of formula (1a) or their prodrugs. The amount of the active ingredient of formula (1) or compound of formula (1a), and/or its and/or its prodrugs in the pharmaceutical compositions can, for example, be from about 5 to 500 mg. The dose of the compounds of this invention, which is to be administered, can cover a wide range. The dose to be administered daily is to be selected to suit the desired effect. A dosage of about 0.001 to 100 mg/kg/day of the compound of formula (1) or compound of formula (1a) or a prodrug thereof may be administered per day. If required, higher or lower daily doses can also be administered.

Actual dosage levels of the active ingredients in the pharmaceutical compositions of this invention can be varied so as to obtain an amount of the active ingredient, which is effective to achieve the desired therapeutic response for a particular patient, composition, and mode of administration without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions.

It is understood that modifications that do not substantially affect the activity of the various embodiments of this invention are included within the invention disclosed herein.

The invention is explained in detail in the examples given below and should not be construed to limit the scope of the invention:

EXAMPLES

The following terms/abbreviations/chemical formulae are employed in the examples:
L: Liter
mL: Milliliter
μL: Microliter
g: Gram
mg: Milligram
μg: Microgram
h: Hours
min: Minutes
lpm: Liters per minute
rpm: Revolutions per minute
RT: Room temperature (25±5° C.)
HPLC: High performance liquid chromatography
TLC: Thin layer chromatography
HOBt: N-Hydroxybenzotriazole
NaOH: Sodium hydroxide
KOH: Potassium hydroxide
HCl: Hydrochloric Acid
DMSO: Dimethyl sulfoxide
RPMI: Roswell Park Memorial Institute
v/v: Volume (of solute) per volume (of solvent).
$IC_{50}$: 50% Inhibitory concentration
$IC_{70}$: 70% Inhibitory concentration
FCS: Fetal calf serum
ATCC: American Type Culture Collection
NCI: National Cancer Institute
DSMZ: Deutsche Sammlung von. Mikroorganismen and Zellkulturen GmbH. (German Collection of Microorganisms and Cell Cultures)
PAA: PAA Laboratories GmbH Preparation of the Compounds Example 1

Step 1

Isolation of Culture No. PM0224355 a) Composition of the medium (CSPYME agar):
Glucose 15 g, corn steep liquor 5 g, peptone 7.5 g, yeast extract 7.5 g, calcium carbonate 2.0 g, sodium chloride 5 g, demineralized water 1.0 L, final pH (at 25° C.) 7.0.

b) Black soil samples were collected from crop fields near village Hosalingpur, Bellary, Karnataka, India and were transferred into sterile plastic bags. The samples were maintained at 4-8° C.

c) Isolation of actinomycetes from this soil:

Soil (about 1 g) was added to sterile demineralized water (10 mL) and the mixture was heated at 55° C. for 6 min, to enrich actinomyces spores and to limit eubacteria. 100 µL of $10^{-3}$ dilution of the heated sample was plated on Corn Starch Peptone Yeast Malt Extract (CSPYME) agar (containing amphotericin B, 20 µg/mL) medium by bulk seed method. Visible colonies were picked after 168 h, purified and were maintained on CSPYME slant for use. The culture was assigned culture no. PM0224355.

Culture no. PM0224355 has been deposited with Microbial Type Culture Collection (MTCC), Institute of Microbial Technology, Sector 39-A, Chandigarh-160 036, India, a World Intellectual Property Organization (WIPO) recognized International Depository Authority (IDA) and has been given the accession number MTCC 5340.

Step 2

Maintenance of Culture No. PM0224355 a) Composition of the medium (ISP2):

Yeast extract 4 g, malt extract 10 g, glucose 4 g, agar 20 g, demineralized water 1.0 L, final pH (at 25° C.) 7.0-7.2.

b) The culture was maintained in glycerol vials at −70° C. for long-term preservation. Periodically its viability was checked using ISP-2 media.

Example 2

Fermentation of PM0224355 Culture in Shake Flasks a) Composition of seed medium:

Glucose 15 g, corn steep liquor 5 g, soybean meal 15 g, calcium carbonate 2 g, sodium chloride 5 g, demineralized water 1.0 L, final pH (at 25° C.) 6.5-7.5.

b) The seed medium (40 mL) was distributed in Erlenmeyer flasks (500 mL) and flasks were autoclaved at 121° C. for 30 min The flasks were cooled to room temperature and each flask was inoculated with a loopful of the well-grown producing strain (culture no. PM0224355) on the slant and was shaken on a rotary shaker for 70-74 h at 230-250 rpm at 30° C. (±1° C.) to obtain the seed culture.

c) Composition of the production medium:

Glycerol 30 g, glucose 3 g, yeast extract 2 g, sodium chloride 3 g, sodium nitrate 1 g, calcium carbonate 3 g, peptone 3 g, trace salt solution 1 mL/L, demineralized water 1.0 L, final pH (at 25° C.) 6.5-7.5.

d) The production medium (200 mL) was distributed in Erlenmeyer flasks (1000 mL) and flasks were autoclaved at 121° C. for 30 min cooled to 29° C.-30° C. and each flask was seeded with 5 mL of the seed culture (as obtained in example 2 (b)).

e) Fermentation parameters:

Temperature 29° C.-30° C., agitation 230-250 rpm, and harvest time 46-50 h.

The harvest pH of the culture broth was 6.0-7.0.

Example 3

Step 1

Extraction of Culture Broth with Ethyl Acetate

The whole broth (1 L) (as obtained in example 2) and was extracted using ethyl acetate (1 L). The organic layer was separated and was concentrated to obtain the crude ethyl acetate extract.

Step 2

Purification of Crude Ethyl Acetate Extract

Crude ethyl acetate extract (as obtained in step 1, example 3) was purified by column chromatography (silica gel, methanol in chloroform). The fractions were monitored by TLC (silica gel, chloroform-methanol 9:1, detection: 254 nm). The fraction eluted with 3% methanol in chloroform, was concentrated to obtain a powder. The powder was crystallized using methanol to obtain a white compound.

$^1$H NMR (DMSO-$d_6$, 500 MHz): δ 6.62 (dd, 1H), 6.26 (s, 1H), 6.12 (dd, 1H), 5.69 (br d, 1H), 5.55 (br d, 1H), 5.31 (ddq, 1H), 5.12 (dd, 1H), 5.11 (br d, 1H), 4.93 (s, 2H) 4.58 (dd, 1H), 4.25 (t, 1H), 4.1 (dd, 1H) 3.90 (t, 1H), 3.88 (m, 1H) 3.82 (dd, 1H), 3.63 (m, 1H), 3.58 (dd, 1H), 3.54 (s, 3H), 3.35 (dq, 1H), 3.32 (br d, 1H), 3.30 (s, 1H), 2.5 (m, 1H), 2.23 (m, 1H), 2.21 (m, 2H), 2.08 (m, 1H) 2.07 (br 3H), 1.90 (m, 1H), 1.84 (br s, 3H), 1.62 (m, 1H), 1.60 (m, 2H), 1.59 (dq, 1H) 1.57 (d, 3H), 1.37 (d, 3H), 1.28 (m, 1H),) 1.23 (m, 2H), 1.12 (d, 3H), 1.10 (d, 3H), 1.07 (d, 3H), 1.01 (d, 3H), 0.89 (t, 3H), 0.82 (d, 3H); MS: m/e 865.

The compound was characterized as concanamycin A by comparison of proton NMR data with the reported data (The Journal of Antibiotics, Vol. 45, No. 7, 1108-1116, (1992)).

The compound obtained in example 3 was used as reference compound.

Example 4

Cultivation of the Culture No PM0224355 in Fermenter

Step 1

Preparation of Seed Culture in Shake Flasks a) Composition of the medium:

Glucose 15 g, corn steep liquor 5 g, soybean meal 15 g, calcium carbonate 2 g, sodium chloride 5 g, demineralized water 1.0 L, pH (at 25° C.) 6.5-7.5.

b) The seed medium (200 mL) was distributed in Erlenmeyer flasks (1000 mL) and flasks were autoclaved at 121° C. for 30 min. The flasks were cooled to room temperature and each flask was inoculated with a loopful of the well-grown producing strain (culture no. PM0224355) on the slant and was shaken on a rotary shaker for 70-74 h at 230-250 rpm at 29° C.-30° C. to obtain the seed culture.

Step 2

Fermentation a) Composition of the production medium:

Glycerol 30 g, glucose 3 g, yeast extract 2 g, sodium chloride 3 g, sodium nitrate 1 g, calcium carbonate 3 g, peptone 3 g, trace salt solution 1 mL/L, demineralized water 1.0 L, pH (at 25° C.) 6.5-7.5.

b) In fermenter (150 L), the above production medium (100 L) along with desmophen (30 mL) as an antifoaming agent was sterilized in situ for 30 min at 121° C., was cooled to 29° C.-30° C. and was seeded with 2.5-3.5 L of the seed culture (as obtained in step 1(b), example 4).

c) Fermentation parameters:

Temperature 29° C.-30° C., agitation 100 rpm, aeration 60 lpm, harvest time 46-50 h. The production of the concanamycin in the fermentation broth was determined by TLC (silica gel, chloroform-methanol 9:1, detection: 254 nm) comparison with reference compound concanamycin A. The harvest pH of the culture broth was 6.0-7.0.

Example 5

Isolation and Purification of Culture Broth PM0224355

Step 1

Extraction

The whole broth (90 L) (as obtained in step 2 (c), example 4) and was extracted using ethyl acetate (90 L). The organic layer was separated and was concentrated to obtain the crude ethyl acetate extract. Yield: 12 g.

Step 2

Purification

Crude ethyl acetate extract (as obtained in step 1, example 5) was purified by column chromatography (silica gel, methanol in chloroform). The fractions were monitored by TLC (silica gel, chloroform-methanol 9:1, detection: 254 nm) using concanamycin A as a reference standard. The fraction which was eluted with 3% methanol in chloroform, was concentrated to obtain extract enriched with concanamycins (5 g). The extract enriched with concanamycins was dissolved in methanol, kept at 4° C. for 10-12 h, and was filtered to obtain a powder (Yield: 0.6 g) which was identified as containing mixture of concanamycin A and concanamycin C by LCMS (molecular weight 865 and 822). This is referred to as concanamycin crude.

Example 6

(3Z,5E,13E,15E)-18-((6E,10E)-3,9-Dihydroxy-4,8-dimethyl-5-oxododeca-6,10-dien-2-yl)-9-ethyl-8,10-dihydroxy-3,17-dimethoxy-5,7,11,13-tetramethyloxacyclooctadeca-3,5,13,15-tetraen-2-one

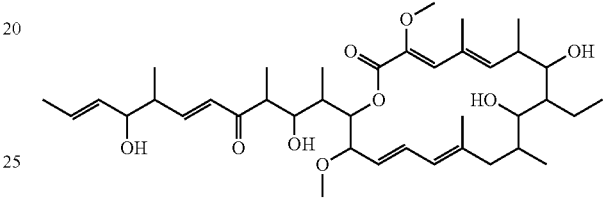

NaOH solution in methanol (0.03M) was added to the powder (100 mg) (as obtained in step 2, example 5) at 10° C. and the mixture was stirred for 20 min. The reaction mixture was neutralized using HCl (1 N) and was extracted with ethyl acetate (3×10 mL). The organic layer was washed with water, dried over sodium sulphate and was concentrated. The crude product was purified by column chromatography (silica gel, 30% ethyl acetate in petroleum ether) to obtain the title compound. Yield: 55 mg.

HPLC: 95% pure [RP-18 (4 mm×250 mm) column, 2-100% gradient of acetonitrile in water over 35 min at 25° C., detection: 220 nm]; MS: m/e 674;

$^1$H NMR (DMSO-$d_6$, 500 MHz): δ 6.77 (dd, 1H), 6.6 (dd, 1H), 6.27 (s, 1H), 6.12 (dd, 1H), 5.67 (br.d, 1H), 5.64 (br.d, 1H), 5.49 (dd, 1H), 5.38 (dd.q, 1H), 5.12 (dd, 1H), 5.10 (dq, 1H), 3.89 (t, 1H), 3.80 (dd, 1H), 3.64 (dd, 1H), 3.53 (s, 3H), 3.48 (t, 1H), 3.23 (s, 3H), 2.97 (br.d, 1H), 2.92 (d, 1H), 2.58 (m, 1H), 2.43 (m, 1H), 2.31 (m, 1H), 1.99 (s, 3H), 1.9 (br.s, 3H), 1.88 (m, 1H), 1.86 (m, 2H), 1.63 (dd, 3H), 1.45 (m, 1H), 1.23 (m, 2H), 1.15 (d, 3H), 1.01 (d, 3H), 1.00 (d, 3H) 0.92 (d, 3H), 0.91 (t, 3H), 0.89 (d, 3H).

$^{13}$CNMR (DMSO-$d_6$, 125 MHz): δ 200.2, 162.4, 147.4, 140.7, 140.4, 140.2, 139.4, 131.7, 131.5, 128.6, 126.6, 125.5, 124.1, 121.3, 80.9, 76.8, 73.3, 72.9, 70.8, 70.0, 58.3, 57.3, 44.8, 44.1, 41.9, 40.9, 37.8, 34.1, 33.3, 20.8, 20.6, 19.2, 16.1, 14.9, 13.8, 12.7, 10.5, 9.0, 7.9.

The compound was characterized as:

(3Z,5E,13E,15E)-18-((6E,10E)-3,9-Dihydroxy-4,8-dimethyl-5-oxododeca-6,10-dien-2-yl)-9-ethyl-8,10-dihydroxy-3,17-dimethoxy-5,7,11,13-tetramethyloxacyclooctadeca-3, 5,13,15-tetraen-2-one, by comparison of proton NMR data with the reported data (Tetrahedron letters, Vol. 22, No. 39, 3857-60, (1981)).

Example 7

(3Z,5E,13E,15E)-18-((5Z,6E,10E)-3,9-Dihydroxy-5-(hydroxymino)-4,8-dimethyl dodeca-6,10-dien-2-yl)-9-ethyl-8,10-dihydroxy-3,17-dimethoxy-5,7,11,13-tetramethyl oxacyclooctadeca-3,5,13,15-tetraen-2-one

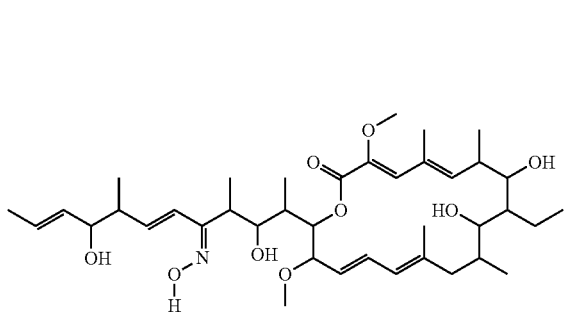 [SMILES: C/C=C/C(O)C(C)/C=C/C(=N\O)C(C)C(O)C(C)C1OC(=O)/C(OC)=C/C(C)=C/C(C)C(O)C(CC)C(O)C(C)C/C(C)=C/C=C/C1OC]

The compound of example 6 (12 mg) was dissolved in the mixture of pyridine (1 mL) and ethanol (1 mL) and was reacted with hydroxylamine hydrochloride (3.17 mg) under nitrogen at 25° C. for 4 h. Water was added to the reaction mixture and the reaction mixture was extracted with ethyl acetate (3×5 mL). The organic layer was washed with water, dried over sodium sulphate and was concentrated. The crude product was purified by column chromatography (silica gel, 40% ethyl acetate in petroleum ether) to obtain the title compound. Yield: 10 mg. HPLC: 99.2% pure, retention time 25.2 min, [RP-18 (4 mm×250 mm) column, 2-100% gradient of acetonitrile in water over 35 min at 25° C., detection: 220 nm]; MS: m/e 689;

$^1$H NMR (DMSO-$d_6$, 500 MHz): δ 10.78 (s, 1H), 6.64 (dd, 1H), 6.54 (dd, 1H), 6.27 (s, 1H), 6.05 (dd, 1H), 5.67 (br d, 1H), 5.62 (d, 1H), 5.49 (dd, 1H), 5.38 (ddq, 1H), 5.25 (d, 1H), 5.09 (dq, 1H), 3.88 (t, 1H), 3.78 (dd, 1H), 3.64 (dd, 1H), 3.48 (s, 3H), 3.48 (t, 1H), 3.42 (s, 3H), 2.97 (br d, 1H), 2.89 (d, 1H), 2.54 (m, 1H), 2.42 (m, 1H), 2.28 (m, 1H), 2.01 (s, 3H), 1.96 (m, 2H), 1.87 (m, 1H), 1.83 (br s, 3H), 1.62 (dd, 3H), 1.47 (m, 1H), 1.23 (m, 2H), 1.07 (d, 3H), 1.01 (d, 3H), 0.99 (d, 3H), 0.94 (d, 3H), 0.91 (t, 3H), 0.85 (d, 3H).

$^{13}$C NMR (DMSO-$d_6$, 125 MHz): δ 164.0, 157.0, 142.3, 141.1, 140.0, 133.7, 133.1, 130.4, 129.5, 127.1, 125.6, 122.9, 120.4, 118.5, 82.9, 78.6, 75.0, 74.7, 72.7, 72.4, 59.4, 55.6, 43.7, 40.4, 39.9, 39.4, 36.1, 35.3, 33.2, 22.7, 22.3, 17.9, 17.8, 16.8, 16.3, 14.4, 12.4, 11.9, 10.7.

Example 7A

The oxime isomers of compound of example 7 were separated on analytical HPLC [silica gel column (250 mm×4 mm) using 2% methanol in chloroform as eluting solvent; 1 ml/min flow rate]. Isomers have retention time of 8.9 mins and 10.2 mins respectively. Both isomers have same molecular weight of 689 and both were found to be equally active in human tumor cell lines.

Example 8

(3Z,5E,13E,15E)-18-((5E,6E,10E)-3,9-Dihydroxy-5-(methoxyimino)-4,8-dimethyl dodeca-6,10-dien-2-yl)-9-ethyl-8,10-dihydroxy-3,17-dimethoxy-5,7,11,13-tetramethyloxacycloocta deca-3,5,13,15-tetraen-2-one

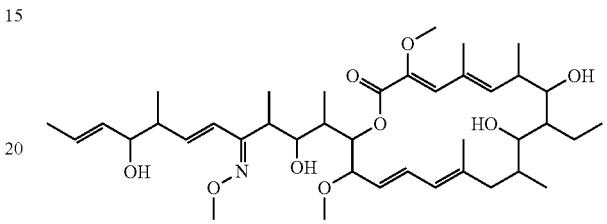

The compound of example 6 (10 mg) was dissolved in the mixture of pyridine (500 μL) and ethanol (500 μL) and was reacted with methoxyamine hydrochloride (6.5 mg) under nitrogen at 25° C. for 4 h. Water was added to the reaction mixture and the reaction mixture was extracted with ethyl acetate (3×5 mL). The organic layer was washed with water, dried over sodium sulphate and was concentrated. The crude product was purified by preparative HPLC [Eurospere-100, C18 column (250 mm×8 mm), mobile phase: acetonitrile-water (1:1 iso cratic)] to obtain the title compound.

Yield: 6.5 mg; MS: m/e: 703.

Example 9

(3Z,5E,13E,15E)-18-((5E,6E,10E)-5-(Benzyloxy-imino)-3,9-dihydroxy-4,8-dimethyldodeca-6,10-dien-2-yl)-9-ethyl-8,10-dihydroxy-3,17-dimethoxy-5,7,11,13-tetramethyloxacycloocta deca-3,5,13,15-tetraen-2-one

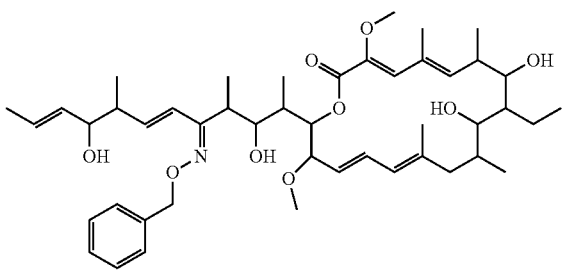 [SMILES: C/C=C/C(O)C(C)/C=C/C(=N\OCc1ccccc1)C(C)C(O)C(C)C1OC(=O)/C(OC)=C/C(C)=C/C(C)C(O)C(CC)C(O)C(C)C/C(C)=C/C=C/C1OC]

The compound of example 6 (10 mg) was dissolved in the mixture of pyridine (300 μL) and ethanol (700 μL) was reacted with benzyloxy amine hydrochloride (8.4 mg) in pyridine under nitrogen at 25° C. for 4 h. Water was added to the reaction mixture and the reaction mixture was extracted with ethyl acetate (3×5 mL). The organic layer was washed with water, dried over sodium sulphate and was concentrated. The crude product was purified by preparative HPLC [Eurospere-

Example 10

((Z)-((6E,10E)-2-((4E,6E,14E,16Z)-11-Ethyl-10,12-dihydroxy-3,17-dimethoxy-7,9,13,15-tetramethyl-18-oxooxacyclooctadeca-4,6,14,16-tetraen-2-yl)-3,9-dihydroxy-4,8-dimethyl dodeca-6,10-dien-5-ylidene)aminooxy)acetic acid

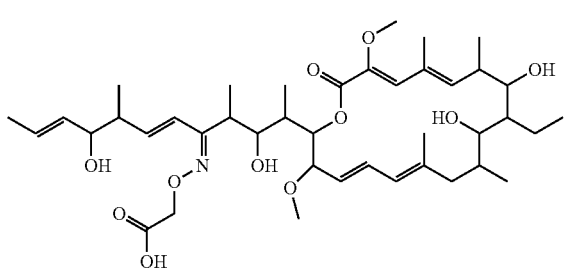 [SMILES: C/C=C/C(O)C(C)/C=C/C(=N\OCC(=O)O)C(C)C(O)C(C)C1OC(=O)/C(OC)=C/C(C)=C/C(C)C(O)C(CC)C(O)C(C)C/C(C)=C/C=C/C1OC]

The compound of example 6 (10 mg) was reacted with carboxymethyl hydroxylamine hemi hydrochloride (4.8 mg) in pyridine (2 mL) and methanol (4 mL) under nitrogen at 25° C. for 14 h. Water was added to the reaction mixture and the reaction mixture was extracted with ethyl acetate (3×5 mL). The organic layer was washed with water, dried over sodium sulphate was concentrated. The crude product was purified by preparative HPLC [Eurospere-100, C18 column (250 mm×8 mm), mobile phase: acetonitrile-water (1:1 isocratic)] to obtain the title compound. Yield: 7.8 mg; MS: m/e 747.

Example 11

(3Z,5E,13E,15E)-18-((5Z,6E,10E)-3,9-Dihydroxy-4,8-dimethyl-5-(2-(4-methyl piperazin-1-yl)-2-oxoethoxyimino)dodeca-6,10-dien-2-yl)-9-ethyl-8,10-dihydroxy-3,17-dimethoxy-5,7,11,13-tetramethyloxacyclooctadeca-3,5,13,15-tetraen-2-one

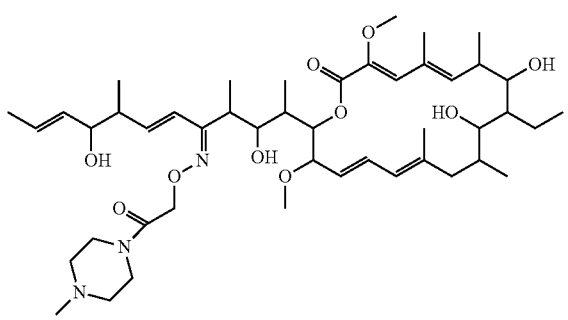 [SMILES: C/C=C/C(O)C(C)/C=C/C(=N\OCC(=O)N1CCN(C)CC1)C(C)C(O)C(C)C1OC(=O)/C(OC)=C/C(C)=C/C(C)C(O)C(CC)C(O)C(C)C/C(C)=C/C=C/C1OC]

To a solution of compound of example 10 (10 mg) in dichloromethane (2 mL) dicyclohexylcarbodiimide (3 mg), and HOBt (2 mg) were added. After 20 min, N-methyl-piperazine (1.5 mg) was added. The reaction mixture was stirred for 18 h under nitrogen atmosphere. Cold water was added to the reaction mixture, the organic layer was separated. The reaction mixture was extracted with dichloromethane (3×5 mL). The combined organic layer was washed with water (2×5 mL). The organic layer was dried over sodium sulphate, and was concentrated. The crude product was purified by preparative HPLC [Eurospere-100, C18 column (250 mm×8 mm), mobile phase: acetonitrile-water (1:1 isocratic)] to obtain the title compound.

Yield: 7.7 mg; ESI-MS: m/e 830 (M+H)⁺.

Example 12

2-((Z)-((6E,10E)-2-((4E,6E,14E,16Z)-11-Ethyl-10,12-dihydroxy-3,17-dimethoxy-7,9,13,15-tetramethyl-18-oxooxacyclooctadeca-4,6,14,16-tetraen-2-yl)-3,9-dihydroxy-4,8-dimethyl dodeca-6,10-dien-5-ylidene)aminooxy)-N-(2-hydroxyethyl)acetamide

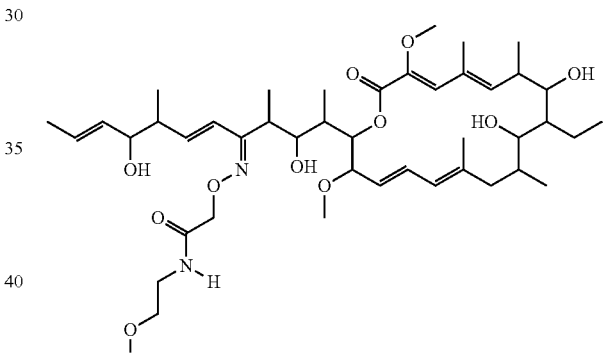

To a solution of compound of example 10 (10 mg) in dichloromethane (2 mL) dicyclohexylcarbodiimide (3 mg), and HOBt (2 mg) were added. After 20 min, ethanol amine (1 mg) was added. The reaction mixture was stirred for 18 h under nitrogen atmosphere. Cold water was added to the reaction mixture, the organic layer was separated. The reaction mixture was extracted with dichloromethane (3×5 mL). The combined organic layer was washed with water (2×5 mL). The organic layer was dried over sodium sulphate, and was concentrated. The crude product was purified by preparative HPLC [Eurospere-100, C18 column (250 mm×8 mm), mobile phase: acetonitrile-water (1:1 isocratic)] to obtain the title compound.

Yield: 5.8 mg; ESI-MS: We 791 (M+H)⁺.

Example 13

(3Z,5E,13E,15E)-18-((5Z,6E,10E)-3,9-Dihydroxy-4,
8-dimethyl-5-(2-oxo-2-(piperidin-1-yl)ethoxyimino)
dodeca-6,10-dien-2-yl)-9-ethyl-8,10-dihydroxy-3,
17-dimethoxy-5,7,11,13-
tetramethyloxacyclooctadeca-3,5,13,15-tetraen-2-
one

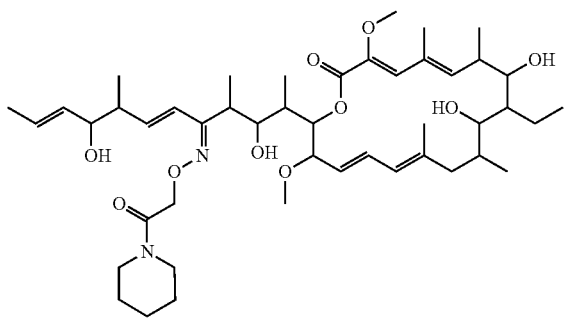 [SMILES: C/C=C/C(O)C(C)/C=C/C(=N\OCC(=O)N1CCCCC1)C(C)C(O)C(C)C1OC(=O)/C(OC)=C/C(C)=C/C(C)C(O)C(CC)C(O)C(C)C/C(C)=C/C=C/C1OC]

To a solution of compound of example 10 (10 mg) in dichloromethane (2 mL) dicyclohexylcarbodiimide (3 mg), and HOBt (2 mg) were added. After 20 min, piperidine (1.3 mg) was added. The reaction mixture was stirred for 18 h under nitrogen atmosphere. Cold water was added to the reaction mixture, the organic layer was separated. Reaction mixture was extracted with dichloromethane (3×5 mL). The combined organic layer was washed with water (2×5 mL). The organic layer was dried over sodium sulphate, and was concentrated. The crude product was purified by preparative HPLC [Eurospere-100, C18 column (250 mm×8 mm), mobile phase: acetonitrile-water (1:1 isocratic)] to obtain the title compound.

Yield: 8.0 mg; ESI-MS: m/e 815 (M+H)$^+$.

Example 14

(3Z,5E,13E,15E)-18-((5Z,6E,10E)-5-(2-(1,4'-Bipip-
eridin-1'-yl)-2-oxoethoxyimino)-3,9-dihydroxy-4,8-
dimethyldodeca-6,10-dien-2-yl)-9-ethyl-8,10-dihy-
droxy-3,17-dimethoxy-5,7,11,13-
tetramethyloxacyclooctadeca-3,5,13,15-tetraen-2-
one

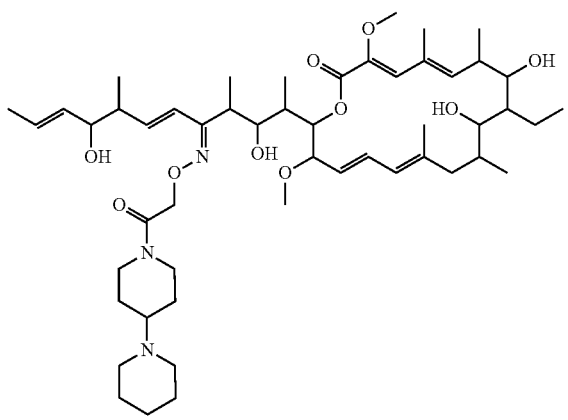 [SMILES: C/C=C/C(O)C(C)/C=C/C(=N\OCC(=O)N1CCC(N2CCCCC2)CC1)C(C)C(O)C(C)C1OC(=O)/C(OC)=C/C(C)=C/C(C)C(O)C(CC)C(O)C(C)C/C(C)=C/C=C/C1OC]

To a solution of compound of example 10 (10 mg) in dichloromethane (2 mL) dicyclohexylcarbodiimide (3 mg), and HOBT (2 mg) were added. After 20 min, 4-piperidino-piperidine 2.5 mg) was added. The reaction mixture was stirred for 18 h under nitrogen atmosphere. Cold water was added to the reaction mixture, the organic layer was separated; Reaction mixture was extracted with dichloromethane (3×5 mL). The combined organic layer was washed with water (2×5 mL). The organic layer was dried over sodium sulphate, and was concentrated. The crude product was purified by preparative HPLC [Eurospere-100, C18 column (250 mm×8 mm), mobile phase: acetonitrile-water (1:1 isocratic)] to obtain the title compound.

Yield: 7.5 mg; ESI-MS: m/e 898 (M+H)$^+$.

Example 15

2-((Z)-((6E,10E)-2-((4E,6E,14E,16Z)-11 Ethyl-10,
12-dihydroxy-3,17-dimethoxy-7,9,13,15-tetram-
ethyl-18-oxooxacyclooctadeca-4,6,14,16-tetraen-2-
yl)-3,9-dihydroxy-4,8-dimethyldodeca-6,10-dien-5-
ylidene)aminooxy)-N-(4-fluorobenzyl)acetamide

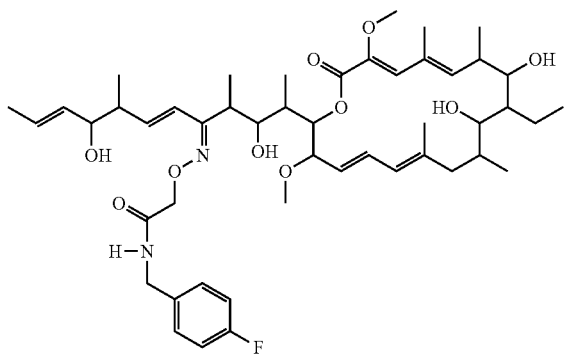 [SMILES: C/C=C/C(O)C(C)/C=C/C(=N\OCC(=O)NCc1ccc(F)cc1)C(C)C(O)C(C)C1OC(=O)/C(OC)=C/C(C)=C/C(C)C(O)C(CC)C(O)C(C)C/C(C)=C/C=C/C1OC]

To a solution of compound of example 10 (10 mg) in dichloromethane (2 mL) dicyclohexylcarbodiimide (3 mg), and HOBt (2 mg) were added. After 20 min. 4-fluoro benzyl amine (1.5 mg) was added, The reaction mixture was stirred for 18 h under nitrogen atmosphere. Cold water was added to the reaction mixture, the organic layer was separated.

The reaction mixture was extracted with dichloromethane (3×5 mL). The combined organic layer was washed with water (2×5 mL). The organic layer was dried over sodium sulphate, and was concentrated. The crude product was purified by preparative HPLC [Eurospere-100, C18 column (250 mm×8 mm), mobile phase: acetonitrile-water (1:1 isocratic)] to obtain the title compound.

Yield: 8.8 mg; ESI-MS: m/e 855 (M+H)$^+$.

Example 16

(2E,6E)-N-(4-((4E,6E,14E,16Z)-11-Ethyl-10,12-dihydroxy-3,17-dimethoxy-7,9,13,15-tetramethyl-18-oxooxacyclooctadeca-4,6,14,16-tetraen-2-yl)-3-hydroxypentan-2-yl)-5-hydroxy-4-methylocta-2,6-dienamide

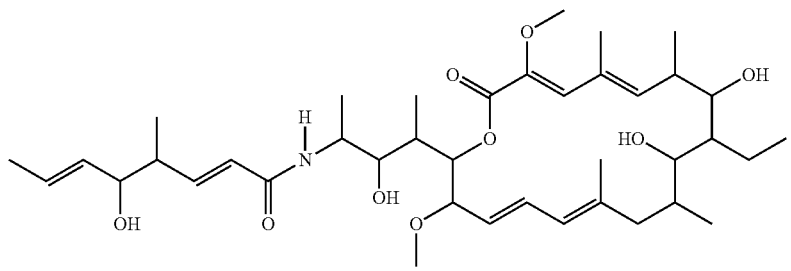 [SMILES: C/C=C/C(O)C(C)/C=C/C(=O)NC(C)C(O)C(C)C1OC(=O)/C(OC)=C/C(C)=C/C(C)C(O)C(CC)C(O)C(C)C/C(C)=C/C=C/C1OC]

The compound of example 7 (3 mg) was dissolved in acetone (1 mL) and was reacted with KOH (1 mg) and tosyl chloride (1.8 mg) under nitrogen at 0° C. for 2 h. Stirring was continued for 1 h at room temperature. Cold water was added to the reaction mixture and the reaction mixture was extracted with ethyl acetate (3×5 mL). The organic layer was washed with water, dried over sodium sulphate, and was concentrated. The crude product was purified by preparative TLC [silica gel, mobile phase: ethyl acetate-hexane (1:1)] to obtain the title compound.

Yield: 0.7 mg. MS: m/e: 689.

Example 17

(3Z,5E,13E,15E)-9-Ethyl-8,10-dihydroxy-3,17-dimethoxy-5,7,11,13-tetramethyl-18-((6E,10E)-3,5,9-trihydroxy-4,8-dimethyldodeca-6,10-dien-2-yl)oxacyclooctadeca-3,5,13,15-tetraen-2-one

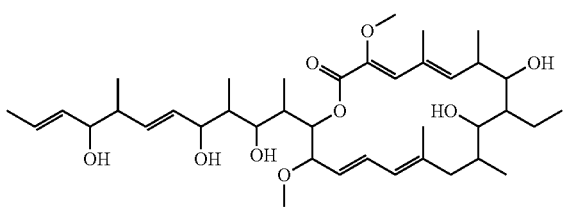 [SMILES: C/C=C/C(O)C(C)/C=C/C(O)C(C)C(O)C(C)C1OC(=O)/C(OC)=C/C(C)=C/C(C)C(O)C(CC)C(O)C(C)C/C(C)=C/C=C/C1OC]

The compound of example 6 (5 mg) was dissolved in tetrahydrofuran (1 mL) and was subjected to reaction with sodium borohydride (0.56 mg) and cerium(III) chloride (CeCl$_3$) (0.9 mg) under nitrogen at 0° C. for 20 min, then was stirred for 20 min at room temperature. Cold water was added to the reaction mixture and it was extracted with ethyl acetate (3×5 mL). The organic layer was washed with water, dried over sodium sulphate and was concentrated. The crude product was purified by preparative TLC [silica gel, mobile phase: hexane-ethyl acetate (1:1)]. to obtain the title compound.

Yield: 2.7 mg; MS: m/e 676.

Biological Testing

Example 18

Monolayer Assay

Step 1

Maintenance of the Cell Lines

Oncotest GmbH, Germany's proprietary tumor cell line panel comprises 40 cell lines. These cell lines were derived from 15 different tumor histotypes, each represented by 1 to 6 different cell lines. Cell lines were established from cancer of the bladder (3), colon (4), head and neck (1), lung (6), breast (3), pancreas (3), prostate (4), ovary (2), kidney (3), liver (1), stomach (1) and the uteri body (1), as well as from melanoma (3), sarcoma (2) and pleuramesothelioma (3). Out of these 40 cell lines, 24 cell lines were established at Oncotest, from patient-derived tumor xenografts. The other 16 cell lines were either provided by the NCI (Bethesda; MD, USA) or were purchased from ATCC (Rockville, Md., USA) or DSMZ (Braunschweig, Germany).

Cell lines were routinely passaged once or twice weekly and maintained in culture for upto 20 passages. All cells were grown at 37° C. in a humidified atmosphere with 5% CO$_2$ in RPMI 1640 medium supplemented with 10% (v/v) fetal calf serum (FCS) and 0.1 mg/mL gentamicin (medium and all other components from PAA, Cölbe, Germany). Authenticity of all cell lines was proven at the DSMZ by STR (short tandem repeat) analysis, a PCR based DNA-fingerprinting methodology.

Step 2

Sample Preparation

Stock solutions of the test compounds (330 µg/mL in DMSO) were prepared and stored in small aliquots (200 µL) at −20° C. An aliquot of the stock solution was thawed on the day of use and stored at room temperature prior to and during dosing. The subsequent dilutions were done with complete RPMI 1640 cell culture medium as follows: the stock solution was diluted 1:22 followed by serial dilutions finally resulting in a (compared to the test concentration) 15-fold higher concentration. For the final dilution step (1:15), 10 μL/well of the respective compound solution was directly added to 140 μL/well culture medium. Test compounds were tested at 0.1-1-10-100-10000 ng/mL. Each concentration was evaluated in triplicate.

Step 3

Assay

A modified propidium iodide assay was used to assess the effect of the test compounds on the growth of the human tumor cell lines and was designed as in reference, Anti-cancer Drugs, 6, 522-532, (1995), the disclosure of which is incorporated by reference for the teaching of the assay.

Cells were plated in 96-well flat-bottom microtiter plates at a cell density of 4,000 to 10,000 cells/well. After a 24 h recovery period to allow the cells to resume exponential growth, the test compounds were applied at five concentrations in log increments in triplicates in two independent runs. After 4 days of treatment, the medium with/without test compounds including all floating (i.e., dead) cells was aspirated and replaced by 200 μL of an aqueous propidium iodide (PI) solution (7 μg/mL). To measure the viable cell number, the remaining adherent cells were killed and permeabilized by repeated freezing and thawing and PI fluorescence was measured using the Cytofluor 4000 microplate reader (excitation λ=530 nm, emission λ=620 nm), which was a measure for the number of cells which survived treatment. Pharmacological effects on cell proliferation and survival were expressed as Test/Control×100 (% T/C) values, with T and C representing the fluorescence read-outs for wells with and without test compound, respectively, i.e. T/C represents the ratio of viable cell numbers following incubation of cell line with/without test compound. Based on the T/C values $IC_{50}$ and $IC_{70}$ values, being the drug concentration necessary to inhibit cell growth by 50% (T/C=50%) and 70% (T/C=30%), respectively, were determined by plotting compound concentration versus cell viability (T/C). IC-values were calculated based on the principle of linear two-point curve fit.

In Vitro Antitumor Activity of Compounds in a Panel of 40 Human Tumor Cell Lines 50% Inhibitory concentration and ($IC_{50}$) and 70% inhibitory concentration ($IC_{70}$) were determined for compound of example 7 by using 40 various human cancer cell lines, specifically, each cell line of bladder cancer (BXF 1218L, BXF 1352L, T-24), colic cancer (CXF 269L, HCT-116, HT-29 and RKO), gastric cancer (GXF 251 L), head and neck cancer (CAL27), Liver cancer (LIXF 575L), non small cell lung cancer (LXF 1121L, LXF 289L, LXF 526L, LXF 529L, LXF 629L and H-460), mammary cancer (MAXF 401NL, MCF-7, MDA-231), melanoma (MEXF 1341L, MEXF 276L, MEXF 462NL), ovary cancer (OVXF 899L and OVCAR-3), pancreatic cancer (PAXF 1657L, PAXF 546L and PANC-1), prostate cancer (22Rv1, DU-145, LNCAP and PC3M), pleuramesothelioma (PXF 1118L, PXF 1752L and PXF 698L), renal cancer (RXF 1781L, RXF 393NL, RXF 486L), Sarcoma (SACS2 and TE671) and uterine cancer (UXF 1138L) was used. The results are indicated in Table 1 and Table 2.

TABLE 1

In vitro antitumor activity of compound of example 7 towards human tumor cell lines
Tumor selectivity towards selected tumor histotypes[1]

| Mean $IC_{70}$ [nm] | Bladder | Colon | Lung | Breast | Melanoma | Prostate | Pleurameso |
|---|---|---|---|---|---|---|---|
| 9.1 | 2/3 | 4/4 | 5/6 | 3/3 | 2/3 | 2/4 | 1/3 |

[1]Number of cell lines among the respective histotype with individual $IC_{70}$ <mean $IC_{70}$

TABLE 2

In vitro antitumor activity of compound of example 7 in a panel of 40 human tumor cell lines

| Cell line | Histotype | $IC_{50}$ [ng/ml] | $IC_{70}$ [ng/ml] |
|---|---|---|---|
| BXF 1218L | Bladder | 4.0 | 46.0 |
| BXF 1352L | Bladder | 0.2 | 2.0 |
| T 24 | Bladder | <0.1 | 0.3 |
| CXF 269L | Colon | <0.1 | 0.2 |
| HCT 116 | Colon | 3.0 | 5.0 |
| HT 29 | Colon | 0.4 | 0.9 |
| RKO | Colon | 0.2 | 0.6 |
| GXF 251 L | Gastric | 1.0 | 6.0 |
| CAL 27 | Head and Neck | <0.1 | 1.0 |
| LIXF 575L | Liver | <0.1 | 2.0 |
| LXF 1121L | Lung | 1.0 | 5.0 |
| LXF 289L | Lung | 6.0 | 68.0 |
| LXF 526L | Lung | <0.1 | 0.1 |
| LXF 529L | Lung | 1.0 | 7.0 |
| LXF 629L | Lung | 0.1 | 1.0 |
| H 460 | Lung | 0.7 | 2.0 |
| MAXF 401NL | Mammary | 3.0 | 8.0 |
| MCF 7 | Mammary | 1.0 | 4.0 |
| MDA 231 | Mammary | <0.1 | <0.1 |
| MEXF 1341L | Melanoma | 0.2 | 2.0 |
| MEXF 276L | Melanoma | 1.0 | 251.0 |
| MEXF 462NL | Melanoma | 3.0 | 6.0 |
| OVXF 899L | Ovarian | 8.0 | 31.0 |
| OVCAR3 | Ovarian | 0.4 | >1000 |
| PAXF 1657L | Pancreas | 8.0 | >1000 |
| PAXF 546L | Pancreas | 0.5 | >1000 |
| PANC 1 | Pancreas | 0.6 | 17.0 |
| 22RV1 | Prostate | 4.0 | 9.0 |
| DU 145 | Prostate | <0.1 | 0.6 |
| LNCAP | Prostate | 3.0 | 15.0 |
| PC3M | Prostate | 0.4 | 3.0 |
| PXF 1118L | Pleuramesothelioma | 432 | >1000 |
| PXF 1752L | Pleuramesothelioma | 3.0 | 22.0 |
| PXF 698L | Pleuramesothelioma | 0.4 | 2.0 |
| RXF 1781L | Renal | 7.0 | 28.0 |
| RXF 393NL | Renal | 7.0 | 1000 |
| RXF 486L | Renal | 16.0 | 39.0 |
| SACS2 | Sarcoma | 5.0 | >1000 |
| TE671 | Sarcoma | 2.0 | 5.0 |
| UXF 1138L | Uterus | 5.0 | 11.0 |
| Mean | | 1.1 | 9.1 |

In Vitro Antitumor Activity of Compounds in a Panel of 12 Human Tumor Cell Lines Mean 50% ($IC_{50}$) and 70% ($IC_{70}$) values were determined for compounds of example 10, 11, 12, 13, 14, 15 [test concentration range 0.0001 μM-10 μM], in a panel of 12 human tumor cell lines, specifically, each cell line of colic cancer (HT-29), gastric cancer (GXF 251 L), lung cancer (LXF 529L, LXF 629L), mammary cancer (MAXF 401NL), melanoma (MEXF 462NL, ovary cancer (OVXF 899L), pancreatic cancer (PAXF 1657L), prostate cancer (22Rv1,), pleuramesothelioma (PXF 1752L), renal cancer (RXF 486L), and uterine cancer (UXF 1138L) cell line was used.

The results are summarized in Table 3.

TABLE 3

In in vitro antitumor activity of compounds in a panel of 12 human tumor cell lines (monolayer assay)

| Sr. No. | Compound | Mean IC$_{50}$ (μM) | Mean IC$_{70}$ (μM) | Selectivity* Total | % Selectivity | Rating** |
|---|---|---|---|---|---|---|
| 01 | Example 10 | 0.514 | 1.258 | 1/12 | 8% | (+) |
| 02 | Example 11 | 0.006 | 0.020 | 3/12 | 25% | (+ + +) |
| 03 | Example 12 | 0.002 | 0.006 | 5/12 | 42% | (+ + +) |
| 04 | Example 13 | 0.030 | 0.097 | 2/12 | 17% | (+ +) |
| 05 | Example 14 | 0.358 | 0.762 | 1/12 | 8% | (+) |
| 06 | Example 15 | 0.001 | 0.003 | 6/12 | 50% | (+++) |

*individual IC$_{70}$ < 1/3 mean IC$_{70}$; for example if mean IC$_{70}$ = 2.1 μM, the threshold for above average sensitivity would be IC$_{70}$< 0.7 μM
**+ (4% > selective >= 12%); ++ (12% > selective >= 20%); +++ (% selective > 20%)

Step 4

Compare Analysis

The Compare Algorithm uses in vitro activity data to obtain information on the probable mode of action (MoA) of a test compound. The individual IC$_{50}$/IC$_{70}$ values of the test compound as obtained in step 3, Example 18, were correlated by a Spearman rank test to the corresponding IC$_{50}$/IC$_{70}$ values for 110 standard agents as determined for these 40 cell lines. These standard agents represent the main MoAs of current anti-cancer drugs Similarities between the activity pattern of a test compound and those of standard drugs are expressed quantitatively as Spearman correlation coefficients. High correlations (ρ>0.6, p<0.05) between the activity patterns of two compounds are indicative of a similar MoA.

CONCLUSIONS

Table 1

The compound of example 7 displayed a remarkable level of tumor selectivity. Cell lines derived from bladder (2 out of 3 tested bladder cancer cell lines showed above-average sensitivity), colon (4/4), lung (5/6) and mammary cancer (2/3), as well as melanoma (2/3) were particularly sensitive. Strong selective activity towards the 4 cell lines derived from colon carcinoma was observed (all 4 colon cancer cell lines displayed IC$_{70}$≤5 ng/ml).

Table 2

Compound of example 7 showed concentration-dependent activity in all cell lines as tested, i.e. cell lines derived from bladder, colon, gastric, head & neck, liver, lung (NSCLC), mammary, ovarian, pancreatic, prostate, renal and uterus cancer, as well as melanoma, pleuramesothelioma and sarcoma. For all 40 cell lines an IC$_{50}$<1 μg/ml was achieved. The overall very strong antitumor potency was evident from a mean IC$_{70}$ value of 9.1 ng/ml. The most sensitive cell lines towards compound of example 8 (IC$_{70}$≤0.3 ng/ml) were found to be T-24 (bladder), CXF 269L (colon), LXFA 526L (lung) and MDA-MB-231 (breast).

Table 3

The compounds of example 10, 11, 12, 13, 14 and 15 showed in vitro antitumor activity in a panel of 12 human tumor cell lines and remarkable level of selectivity.

Compare Analysis

IC$_{70}$ based Compare Analysis revealed significant correlations of compound of example 7 to the HDAC inhibitors Trichostatin A (Spearman correlation coefficient ρ=0.62) and Depsipeptide (ρ=0.61). Correlations at a lower level were found to the HDAC inhibitor Apicidin (ρ=0.57) and to the antimetabolites Alimta (ρ=0.58) and Methotrexate (ρ=0.56).

We claim:

1. A compound of formula (1) having a stereochemical configuration of concanamycin, or a pharmaceutically acceptable salt thereof,

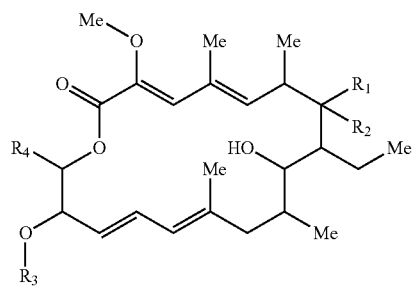

Formula (1)

wherein
R1 is hydroxy or alkoxy;
R2 is hydrogen;
R3 is methyl;
R4 is selected from the following formulae:

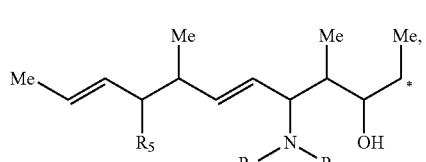

Formula (2)

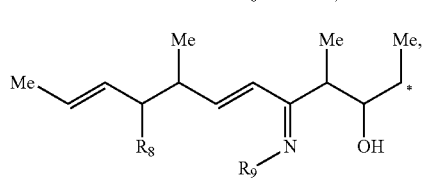

Formula (3)

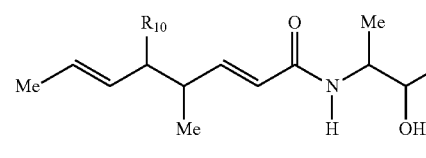

Formula (6)

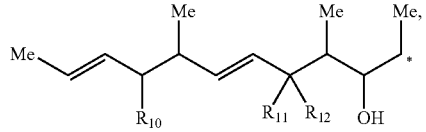

Formula (7)

* indicates point of attachment;
R5 is hydroxy;
R6 is hydrogen;
R7 is hydrogen;
R8 is hydroxy;

R9 is selected from hydroxy, alkyl, alkoxy, aryl, aralkyl, aryloxy, benzyloxy, heterocyclyl, —O-heterocyclyl, —OCH2COOR17 and —OCH2COR18;
R10 is hydroxy;
R11 is hydrogen;
R12 is hydroxy;
R17 is hydrogen or alkyl;
R18 is selected from alkyl, —NHCH2R20, aryl and heterocyclyl; and
R20 is selected from hydrogen, alkyl, aryl and heterocyclyl;
where alkyl is unsubstituted or substituted by one or two of the same or different groups selected from: hydroxy, halogen, amino, hydroxyalkyl, alkoxy, aryl, aryloxy and heterocyclyl;
alkoxy is unsubstituted or substituted by one or two of the same or different groups selected from: halogen, hydroxy, alkyl and hydroxyalkyl;
aryl is unsubstituted or substituted by one or two of the same or different groups selected from: halogen, hydroxy, amino, alkyl, hydroxyalkyl, alkoxy, aryl and heterocyclyl;
heterocyclyl is unsubstituted or substituted by one or two of the same or different groups selected from: halogen, hydroxy, amino, alkyl, hydroxyalkyl, alkoxy, aryl and heterocyclyl.

2. A compound according to claim 1, or a pharmaceutically acceptable salt thereof, wherein
R1 is hydroxy or alkoxy;
R2 is hydrogen;
R3 is methyl;
R4 is selected from the following formulae:

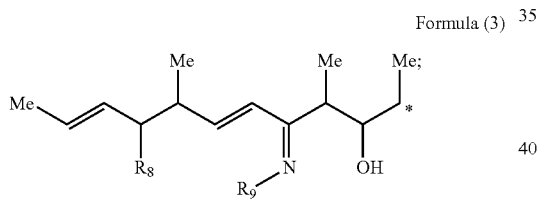

Formula (3)

and

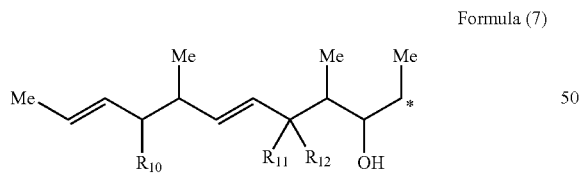

Formula (7)

* indicates point of attachment;
R8 is hydroxy;
R9 is selected from hydroxy, alkyl, alkoxy, aryl, aralkyl, aryloxy, benzyloxy, heterocyclyl, —O-heterocyclyl, —OCH2COOR17 and —OCH2COR18;
R10 is hydroxy;
R11 is hydrogen
R12 is hydroxy;
R17 is hydrogen or alkyl;
R18 is selected from alkyl, —NHCH2R20, aryl and heterocyclyl; and
R20 is selected from hydrogen, alkyl, aryl, and heterocyclyl;

where alkyl is unsubstituted or substituted by one or two of the same or different groups selected from: hydroxy, halogen, amino, hydroxyalkyl, alkoxy, aryl, aryloxy and heterocyclyl;
alkoxy is unsubstituted or substituted by one or two of the same or different groups selected from: halogen, hydroxy, alkyl and hydroxyalkyl;
aryl is unsubstituted or substituted by one or two of the same or different groups selected from: halogen, hydroxy, amino, alkyl, hydroxyalkyl, alkoxy, aryl and heterocyclyl;
heterocyclyl is unsubstituted or substituted by one or two of the same or different groups selected from: halogen, hydroxy, amino, alkyl, hydroxyalkyl, alkoxy, aryl and heterocyclyl.

3. A compound according to claim 1, or a pharmaceutically acceptable salt thereof, wherein
R1 is hydroxy;
R2 is hydrogen;
R3 is methyl;
R4 is formula (3):

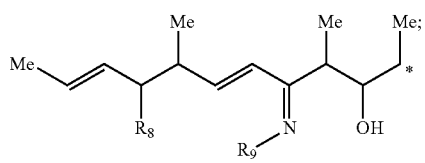

* indicates point of attachment;
R8 is hydroxy; and
R9 is selected from hydroxy, alkyl, alkoxy and benzyloxy;
where alkyl is unsubstituted or substituted by one or two of the same or different groups selected from: hydroxy, halogen, amino, hydroxyalkyl and alkoxy.

4. A compound according to claim 3, or a pharmaceutically acceptable salt thereof, wherein
R1 is hydroxy;
R2 is hydrogen;
R3 is methyl;
R4 is formula (3):

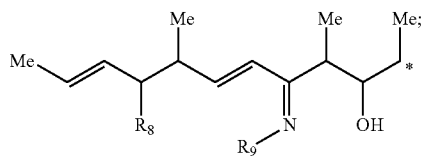

* indicates point of attachment;
R8 is hydroxy; and
R9 is selected from hydroxy, methoxy and benzyloxy.

5. A compound according to claim 4, or a pharmaceutically acceptable salt thereof, wherein
R1 is hydroxy;
R2 is hydrogen;
R3 is methyl;
R4 is formula (3):

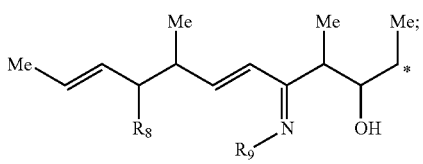

* indicates point of attachment;
R8 is hydroxy; and
R9 is hydroxy.

6. A compound according to claim 1, or a pharmaceutically acceptable salt thereof, wherein
R1 is hydroxy or alkoxy;
R2 is hydrogen;
R3 is methyl;
R4 is formula (3):

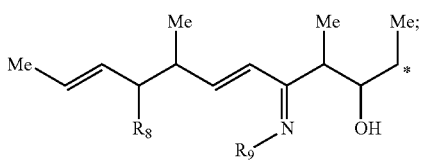

* indicates point of attachment;
R8 is hydroxy;
R9 is —OCH2COOR17 or —OCH2COR18;
R17 is hydrogen or alkyl;
R18 is selected from alkyl, heterocyclyl and —NHCH2R20; and
R20 is selected from hydrogen, alkyl, aryl and heterocyclyl;
where alkyl is unsubstituted or substituted by one or two of the same or different groups selected from: hydroxy, halogen, amino, hydroxyalkyl and alkoxy;
alkoxy is unsubstituted or substituted by one or two of the same or different groups selected from: hydroxy, alkyl and hydroxyalkyl;
aryl is unsubstituted or substituted by one or two of the same or different groups selected from: halogen, hydroxy, hydroxyalkyl, alkoxy, aryl and heterocyclyl;
heterocyclyl is unsubstituted or substituted by one or two of the same or different groups selected from: hydroxy, hydroxyalkyl, alkyl, alkoxy, aryl and heterocyclyl.

7. A compound according to claim 6, or a pharmaceutically acceptable salt thereof, wherein
R1 is hydroxy;
R2 is hydrogen;
R3 is methyl;
R4 is formula (3):

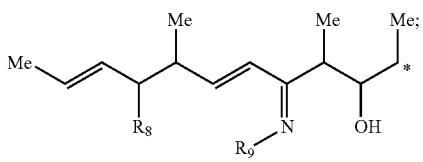

* indicates point of attachment;
R8 is hydroxy;
R9 is —OCH2COOR17; and
R17 is hydrogen or alkyl.

8. A compound according to claim 6, or a pharmaceutically acceptable salt thereof, wherein
R1 is hydroxy;
R2 is hydrogen;
R3 is methyl;
R4 is formula (3):

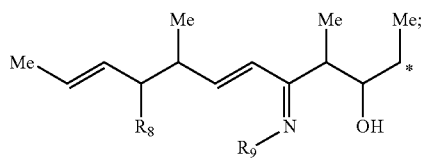

* indicates point of attachment;
R8 is hydroxy;
R9 is —OCH2COR18; and
R18 is selected from 4-methylpiperazin-1-yl, piperidin-1-yl and 1,4'-bipiperidin-1'-yl.

9. A compound according to claim 6, or a pharmaceutically acceptable salt thereof, wherein
R1 is hydroxy;
R2 is hydrogen;
R3 is methyl;
R4 is formula (3):

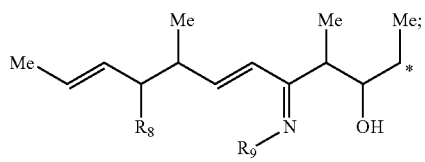

* indicates point of attachment;
R8 is hydroxy;
R9 is —OCH2COR18;
R18 is —NHCH2R20; and
R20 is alkyl or aryl;
where alkyl is unsubstituted or substituted by one or two of the same or different groups selected from: hydroxy, halogen, amino, hydroxyalkyl and alkoxy;
aryl is unsubstituted or substituted by one or two of the same or different groups selected from: halogen, hydroxy and alkoxy.

10. A compound according to claim 9, or a pharmaceutically acceptable salt thereof, wherein
R1 is hydroxy;
R2 is hydrogen;
R3 is methyl;
R4 is formula (3):

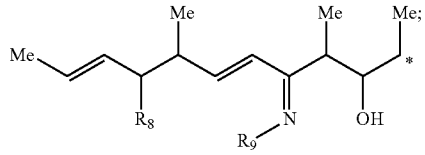

* indicates point of attachment;
R8 is hydroxy;
R9 is —OCH2COR18;
R18 is —NHCH2R20; and
R20 is —CH2OH or 4-fluorophenyl.

11. A compound according to claim 1, or a pharmaceutically acceptable salt thereof, wherein
R1 is hydroxy or alkoxy;
R2 is hydrogen;
R3 is methyl;
R4 is formula (6):

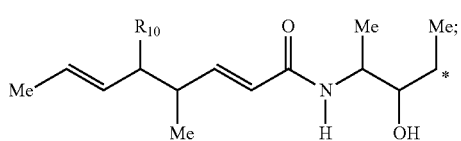

* indicates point of attachment;
R10 is hydroxy.

12. A compound according to claim 11, or a pharmaceutically acceptable salt thereof, wherein
R1 is hydroxy;
R2 is hydrogen;
R3 is methyl;
R4 is formula (6):

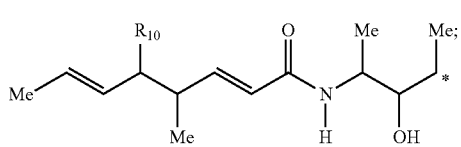

* indicates point of attachment;
R10 is hydroxy.

13. A compound according to claim 1, or a pharmaceutically acceptable salt thereof, wherein
R1 is hydroxy or alkoxy;
R2 is hydrogen;
R3 is methyl;
R4 is formula (7):

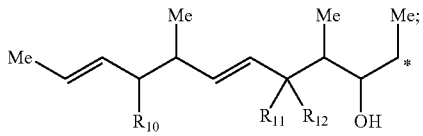

* indicates point of attachment;
R10 is hydroxy;
R11 is hydrogen; and
R12 is hydroxy.

14. A compound according to claim 13, or a pharmaceutically acceptable salt thereof, wherein
R1 is hydroxy;
R2 is hydrogen;
R3 is methyl;
R4 is formula (7):

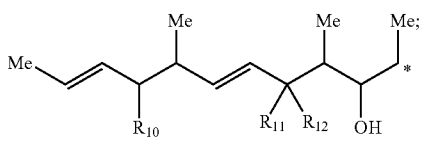

indicates point of attachment;
R10 is hydroxy;
R11 is hydrogen; and
R12 is hydroxy.

15. A compound according to claim 1, or a pharmaceutically acceptable salt thereof, wherein the compound is:

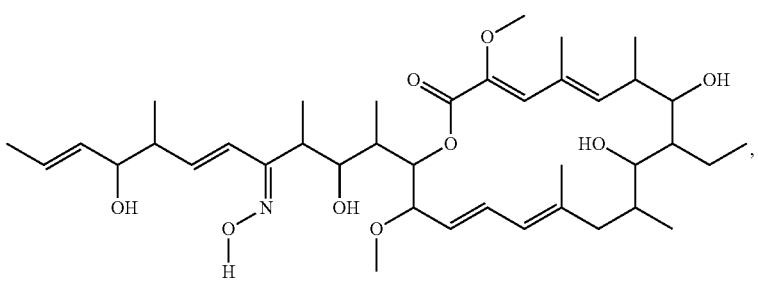

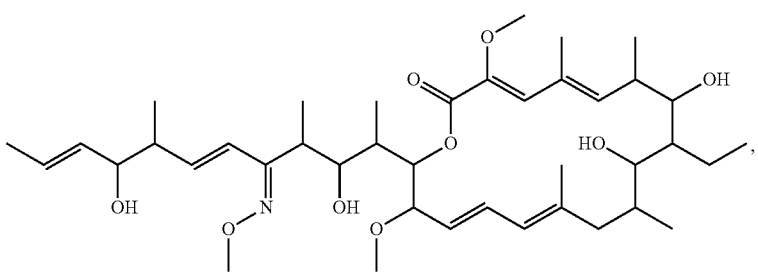

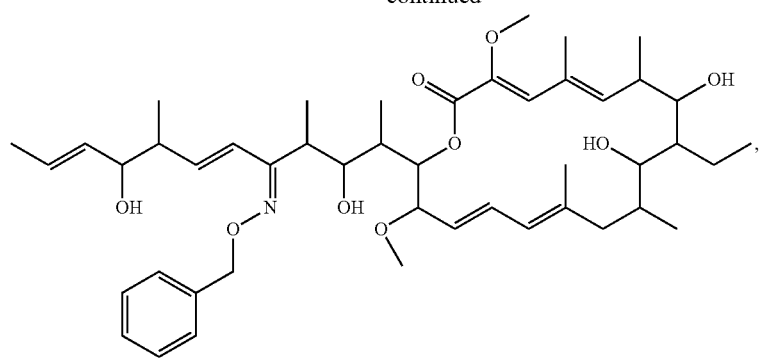
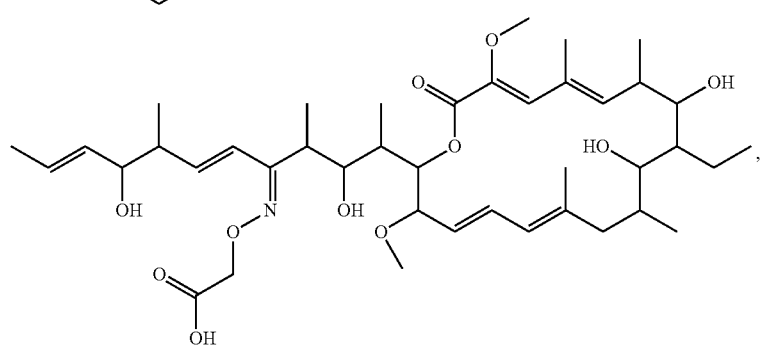
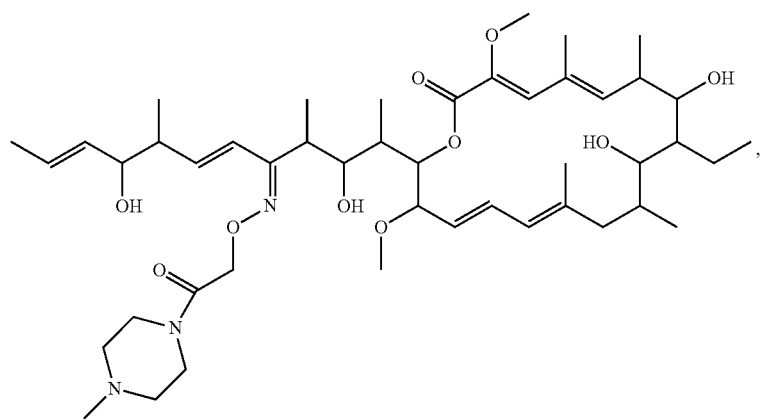
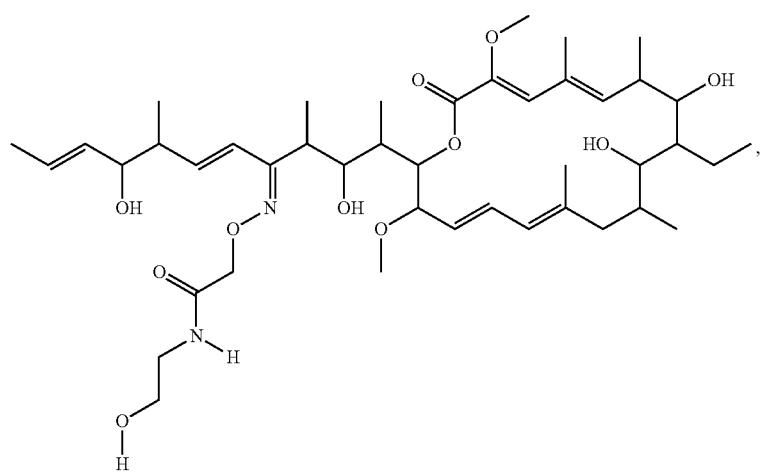

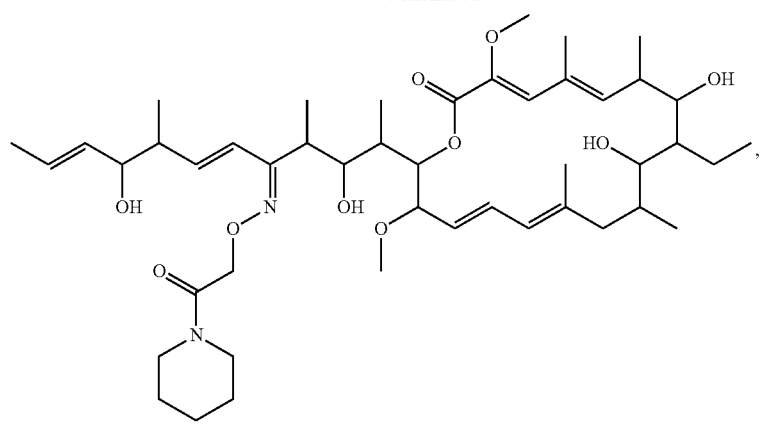
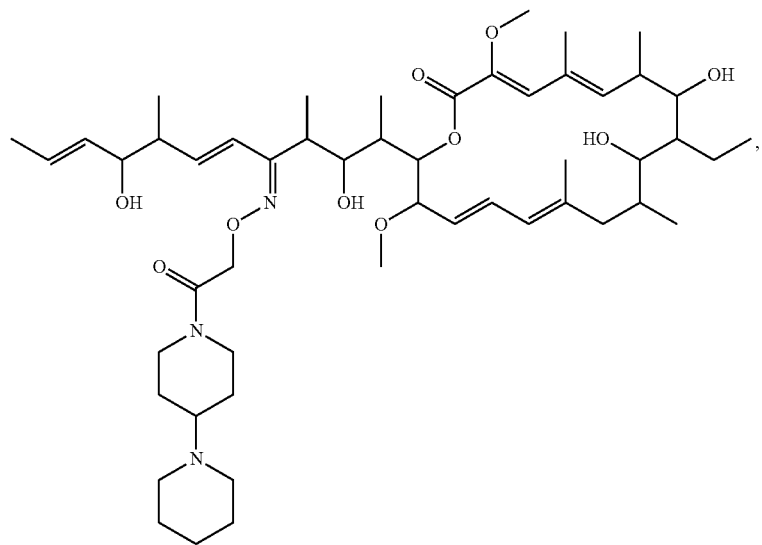
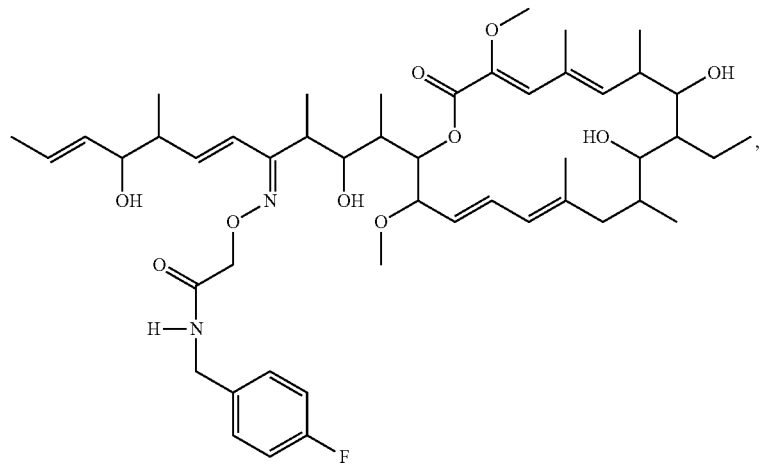
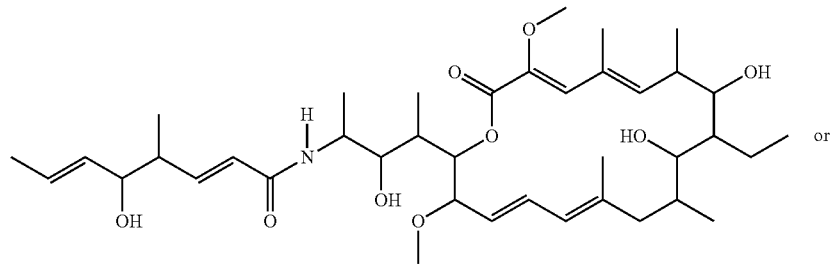
or

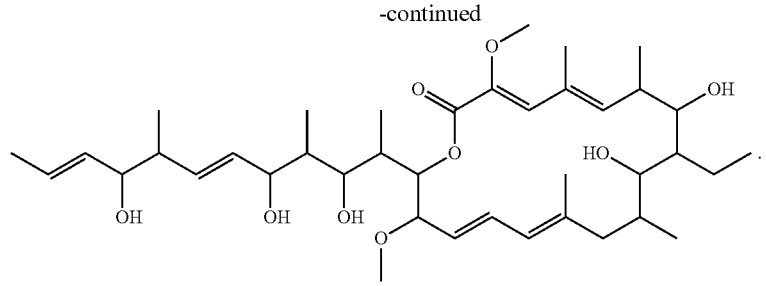

16. A pharmaceutical composition, comprising a therapeutically effective amount of one or more compounds of formula (1) according to claim 1, or a pharmaceutically acceptable salt thereof, and a pharmaceutically acceptable carrier or diluent.

17. A method for the treatment of cancer comprising administering to a mammal in need thereof a therapeutically effective amount of one or more compounds of formula (1) according to claim 1, or a pharmaceutically acceptable salt thereof.

* * * * *